United States Patent
Fu et al.

(10) Patent No.: US 9,333,215 B2
(45) Date of Patent: May 10, 2016

(54) AQUEOUS SOLUTION OF 20(R)-GINSENOSIDE RG3 PHARMACEUTICAL COMPOSITION AND PROCESS THEREOF

(71) Applicant: Li Fu, Dalian (CN)

(72) Inventors: Li Fu, Liaoning (CN); Qi Lu, Dalian (CN)

(73) Assignee: Li Fu, Dalian (CN)

( * ) Notice: Subject to any disclaimer, the term of this patent is extended or adjusted under 35 U.S.C. 154(b) by 0 days.

(21) Appl. No.: 13/941,106

(22) Filed: Jul. 12, 2013

(65) Prior Publication Data
US 2013/0345156 A1    Dec. 26, 2013

Related U.S. Application Data

(62) Division of application No. 12/301,996, filed on May 11, 2010, now Pat. No. 8,487,090.

(30) Foreign Application Priority Data

May 22, 2006   (CN) .......................... 2006 1 0046617
May 18, 2007   (WO) ...................... PCT/CN07/01635

(51) Int. Cl.
| | |
|---|---|
| *A61K 31/704* | (2006.01) |
| *A61K 9/00* | (2006.01) |
| *A61K 9/08* | (2006.01) |
| *A61K 9/19* | (2006.01) |
| *A61K 47/40* | (2006.01) |
| *A61K 47/48* | (2006.01) |
| *B82Y 5/00* | (2011.01) |

(52) U.S. Cl.
CPC ............ *A61K 31/704* (2013.01); *A61K 9/0019* (2013.01); *A61K 9/08* (2013.01); *A61K 9/19* (2013.01); *A61K 47/40* (2013.01); *A61K 47/48969* (2013.01); *B82Y 5/00* (2013.01)

(58) Field of Classification Search
None
See application file for complete search history.

(56) References Cited

FOREIGN PATENT DOCUMENTS

| | | |
|---|---|---|
| CN | 1393484 | 1/2003 |
| CN | 1526405 | 9/2004 |
| CN | 1569011 | 1/2005 |
| CN | 1569012 | 1/2005 |

OTHER PUBLICATIONS

Paek, K. et al "Large scale culture of ginseng adventitious roots . . . " Adv. Biochem. Engin./Biotechnol. (2009) vol. 113, pp. 151-176.*
Wan, H. et al "Highly efficient biotransformation of ginsenoside . . . " RSC Adv. (2015) vol. 5, pp. 78874-78879.*
International Search Report for appl. No. PCT/CN2007/001635, mailed Aug. 16, 2007, 8 pgs.
Supplementary European Search Report for appl. No. EP 07721208, mailed Dec. 17, 2012, 8 pgs.
Qian et al., "In vivo rat metabolism and pharmacokinetics studies of ginsenoside Rg3" J. Chromatog. B vol. 816, pp. 223-232 (2005).
Machine translation of published application CN 2006-10047600 (Apr. 18, 2007).
Dialog machine translation of CN 1393484 (2003).
Dialog machine translation of CN 1526405 (2004).
Del Valle "Cyclodextrins and their uses: a review" Proc. Biochem. (2004) vol. 39, pp. 1033-1046.
Gokce et al., "L-Arginine and hypertension" J. Nutr. vol. 134, pp. 2807S-2811S (2004).

* cited by examiner

*Primary Examiner* — Leigh C Maier
(74) *Attorney, Agent, or Firm* — Squire Patton Boggs (US) LLP

(57) ABSTRACT

A preparation of a kind of 20(R)-ginsenoside Rg3 medicinal composition aqueous solution containing ginsenoside Rg3 0.5~10 mg/ml: add 0.1-5% of ginsenoside solution to 0.1~30% of adjuvant A, B①②⑤ at the temperature of 40~100° C., the ratio of these two is 1:1~300, add water after the solvent is recycled under reduced pressure; another kind of 20(R)-ginsenoside Rg3 medicinal composition aqueous solution contains 0.1~2 mg/ml of 20 (R) of the ginsenoside Rg3, the preparation: add 0.1~5% of ginsenoside solution to 20~65% of adjuvant B③④ at the temperature of 60~100° C., main material to adjuvant B=1:100~400, add water after the solvent is recycled under reduced pressure. The above 20 (R) ginsenoside Rg3 composition aqueous solution and the powder after lyophilization can be used to prepare injectable, oral administration and external use, and the bioactivity of these preparations is high, and with the actions of anti cancer, efficacy potentiation and toxicity attenuation effects of the combined chemical or radiation therapy of tumor, enhancement of human immune functions, improvement of human memory, anti fatigue, and detumescence, pain relieving.

6 Claims, 11 Drawing Sheets

AQUEOUS SOLUTION OF 20(R)-GINSENOSIDE RG3 PHARMACEUTICAL COMPOSITION AND PROCESS THEREOF

CROSS-REFERENCE TO RELATED APPLICATIONS

This application is a divisional application of U.S. application Ser. No. 12/301,996 having filing date or 371(c) date May 11, 2010, which is a national phase application of PCT/CN2007/001635 filed on May 18, 2007, which claims priority to Chinese Application No. 200610046617.2 filed on May 22, 2006, the teachings of which are incorporated by reference in their entirety.

TECHNOLOGICAL FIELD OF THE INVENTION

This invention relates to a ginsenoside Rg3 pharmaceutical composition and process thereof.

TECHNOLOGICAL BACKGROUND OF THE INVENTION

Ginsenoside Rg3 is a tetracyclic-triterpene saponin compound existed in Ginseng, with a molecular weight of 784.13. There are two optical isomers for ginsenoside Rg3, ie. 20(R)-ginsenoside Rg3 and 20(S)-ginsenoside Rg3. 20(R)-ginsenoside Rg3 is chemically stable, and insoluble in water, while 20(S)-ginsenoside Rg3 is chemically unstable, and easily dissolvable in water. Their molecular structures are as follows:

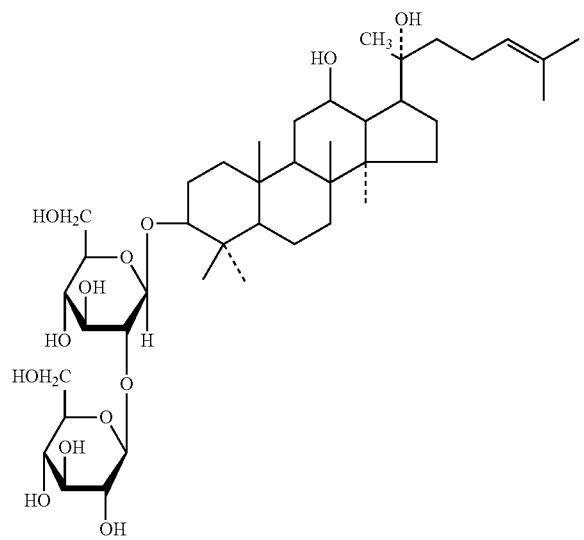

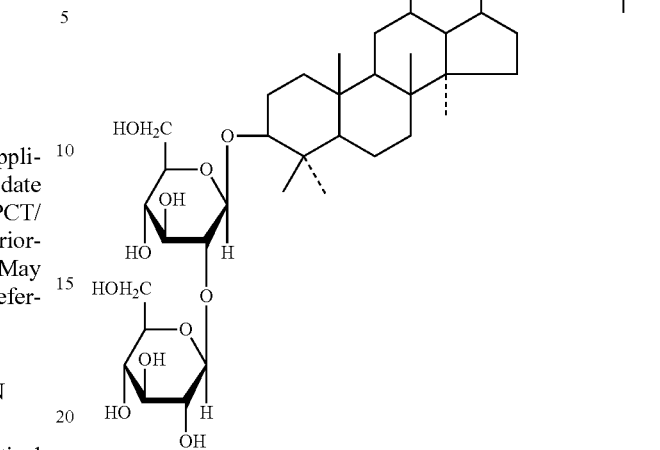

The Molecular Structure of 20(R)-ginsenoside Rg3. The Molecular Structure of 20(S)-ginsenoside Rg3.

It is found that 20(R)-ginsenoside Rg3 has strong inhibitory and anti-metastatic activities to the tumor. As 20(R)-ginsenoside Rg3 is insoluble in water; the bioavailability of its oral preparations is very low, which greatly restricts the fulfillment of its clinical efficacy and its parenteral route of administration.

To dissolve the 20(R)-ginsenoside Rg3 in water, some studies have been explored, such as "Ginsenoside Rg3 hydroxypropyl-β-cyclodextrin clathrate, preparations and its processes" (Application No. 01119929.6), which was published in the Patent Bulletin on Jan. 29, 2003. The main content of the patent is as follows: Ginsenoside Rg3 hydroxypropyl-β-cyclodextrin clathrate, with a raw material weight ratio of ginsenoside:hydroxypropyl-β-cyclodextrin=1:1~200. The preparation process as follows: (1) Dissolve the ginsenoside Rg3 in organic solvent; (2) Dissolve the hydroxypropyl-β-cyclodextrin in water; (3) Drip the ginsenoside solution to the hydroxypropyl-β-cyclodextrin solution, with vigorous stirring; after that continue stirring the mixture for another 2~24 hours. Filter the mixture with a 0.45 μm micropore filter membrane, condense the filtrate, remove the organic solvent, redissolve in water for injection, and then filter the filtrate again with a 0.22 μm micropore filter membrane, lyophilize the filtrate to get a porous white powder, i.e. the ginsenoside clathrate.

The shortcomings of the method are as follows: (1) In the process of clathrate preparation, when the reactant (reactant solution) is recycled to a third of its original volume, there is still some residue of the organic solvent detected; however, it is ineffective to remove the residual organic solvent by lyophilization. Therefore, it is very difficult to meet the specification of the residual solvent in an injection solution when it is prepared with this clathrate powder. (2) In the process of clathrate preparation, the residual solvent is very helpful to form a dissolvable clathrate of ginsenoside Rg3 and hydroxypropyl-β-cyclodextrin, with a ratio of 1:1~200. If the residual solvent is completely removed, there will be no stable clathrate formed under the above-mentioned range of ratio, and the ginsenoside Rg3 will be immediately separated as sediment from the aqueous clathrate, leaving the clathrate unsuitable for the preparation of injection solution. (3) Ginsenoside Rg3 could not be transformed to the clathrate completely with this method, and the utilization rate of the Rg3 is only 86%. Therefore, the cost of the production for making injection solution will be increased obviously.

DESCRIPTION OF THE INVENTION

The objectives of this invention are to provide a preparation process and the medicinal usage for the 20(R)-ginsenoside Rg3 pharmaceutical composition and its pharmaceutical preparations, with characteristics of low production cost and easy absorption (high bioavailability) of human body.

The main raw material (for short, main material) of this invention is 20(R)-ginsenoside Rg3, and the adjuvant material (for short, adjuvant) of this invention is composed of Class A and Class B materials. Class A includes deoxycholic acid (sodium), sodium dodecylsulphate (SDS) and arginine; Class B is cyclodextrins including (1) cyclodextrin and its derivates, such as polymerized cyclodextrin nanoscale microparticle, polymerized cyclodextrin and side chained cyclodextrin (B ①); (2) β-cyclodextrin and its derivates, such as β-cyclodextrin, 2,6-dimethyl-β-cyclodextrin, glucosyl-β-cyclodextrin, nano based β-cyclodextrin, sulfobutyl ether β-cyclodextrin, methyl-β-cyclodextrin and non-localized methylated-β-cyclodextrin (B ②); (3) hydroxypropyl-β-cyclodextrin and its derivates, such as 2-hydroxypropyl-β-cyclodextrin, 3-hydroxypropyl-β-cyclodextrin derivates, 2,3-dihydroxypropyl-β-cyclodextrin, and 2,3,6-trihydroxypropyl-β-cyclodextrin (B ③); (4) hydroxyethyl-β-cyclodextrin (B ④); and (5) an adjuvant mixture of cyclodextrin and its derivates, i.e. the mixture mixed by different combinations of above-mentioned cyclodextrin, β-cyclodextrin, hydroxypropyl-β-cyclodextrin, hydroxyethyl-β-cyclodextrin, and their derivates (B ⑤).

The weight ratio of main material to adjuvant materials is as follows:

20(R)-ginsenoside Rg3:adjuvant A or B ①, ②, ⑤=1:1~300; and 20(R)-ginsenoside Rg3:adjuvant B ③, ④=1:100~400.

A preparation process of 20(R)-ginsenoside Rg3 pharmaceutical composition is as follows:

(1) Preparation of main material solution: Dissolve the 20(R)-ginsenoside Rg3 in an organic solvent mixture to make a 0.1~5.0% ginsenoside solution. The name and proportion of the mixed organic solvents are as follows: 1) chloroform: ethyl acetate:ethanol (methanol):water=10-25:30~45:18~30: 5~15, lower level; 2) chloroform:ethanol (methanol):water=70~60:40~30:10, lower level; 3) ethanol:water=90~95: 10~5; 4) methanol:water=85~90:15~10; 5) acetonitrile: water=40~60:60~40; 6) Dichloromethane:ethanol (methanol):water=60~65:40~35:10; 7) acetonitrile:ethanol (methanol)=70~80:30~20; 8) dimethyl sulfoxide:water=90~80:10~20; and 9) propylene glycol:ethanol (methanol):Tween 80:water=40~50:10~20:1:49~29.

(2) Preparation of adjuvant material solution: 1) Dissolve the above-mentioned Class A and Class B adjuvant in water individually to make a 0.1~30% aqueous solution (a); 2) Dissolve the above-mentioned Class B ③ and ④ subgroup adjuvant in water individually to make a 20~65% aqueous solution (b).

(3) Adding main material solution into adjuvant solution: 1) directly add the above-mentioned ginsenoside solution into the adjuvant solution (a) at 40~100° C. and stir the mixture for 0.3~1 hour, and then obtain a clear solution. or 2) Drip the above-mentioned ginsenoside solution at a constant rate into adjuvant solution (b) at 60~100° C. and stir the aqueous solution until the dripping is complete, and then a clear solution is obtained.

(4) Recycling the solvent and prepare the pharmaceutical composition: Recycle the solvent by decompressing the clear solution in step (3) into a near dryness state about ⅔ of its original volume, with a degree of vacuum of 0.01~0.08 MPa, at temperature of 80~100° C. Reconstitute the solution by adding water to the original volume and recycle the solvent by decompressing into near dryness; repeat the above-mentioned procedure twice, and finally reconstitute the nearly dried material by adding water for injection or purified water, and then mix well for dissolving. The resultant aqueous solution is the 20(R)-ginsenoside Rg3 pharmaceutical composition. For the composition solution made from 20(R)-ginsenoside Rg3 and adjuvant of Class A or Class B①, ②, and ⑤, the content of main material is 0.5~10 mg/mL; for the composition solution made from 20(R)-ginsenoside Rg3 and adjuvant Class B③ and ④, the content of main material is 0.1~2 mg/mL. Following drying processes such as vacuum, spray or lyophilization, the water-soluble pharmaceutical composition powder of 20(R)-ginsenoside Rg3 can be obtained, and the drying method and conditions are as follows:

| Drying method | Drying conditions |
| --- | --- |
| Vacuum drying | Temperature, 30~60° C.; Pressure, 0.01~08 MPa, Vacuum Drying for 48 hours |
| Spray drying | Supersonic jet flow technology is used. Jet flow rate, 300~990 m/s; Temperature, 30~60° C.; Pressure, 0.01~0.05 MPa, instant drying at supersonic speed. |
| Lyophilizing (freeze drying) | Pre-freeze for 5 hours at −45° C., and lyophilize following a temperature gradient program: −45° C.~−15° C., sublimation drying for 20 hours, and then vacuum drying for 10 hours at −15~30° C. |

With this water-soluble 20(R)-ginsenoside Rg3 pharmaceutical composition as raw material, following different kinds of preparations could be prepared:

(1) Preparations for oral and external application: For the 20(R)-ginsenoside Rg3 composition solution obtained by reaction of main material with adjuvant Class A and B, water-soluble ginsenoside Rg3 solid powder can be produced by drying process. After formulated with pharmaceutically receivable carriers and processed by pharmaceutical techniques, different kinds of preparations can be produced, such as granules, tablets (general tablet, dispersion tablet, delay released tablet, controlled release tablet, etc), soft or hard capsules, oral application solution, external application preparations (patch, ointment, dropping, and aerosol).

(2) Injectable preparations: For the 20(R)-ginsenoside Rg3 composition solution obtained by reaction of main material with adjuvant Class A and Class B ° C. and ° C.: 1) uniformly mix the above-mentioned 20(R)-ginsenoside Rg3 composition aqueous solution either via an ultrafilter or by adding 0.1% (weight) medicinal injection grade active carbon, leave it at 80° C. for 30 minutes, remove the pyrogen by filtering with a 0.45 μm micropore filter membrane. Following sterilization via a 0.22 μm micropore filter membrane a injection solution is obtained. Or following lyophilization, lyophilized powder for injection or sterile powder for injection is obtained. 2) Dry and recycle solvent from the above-mentioned aqueous solution by either lyophilization, vacuum dryness or spraying to make a stable and water soluble ginsenoside Rg3 solid powder. Following reconstitution, the lyophilized powder for injection or sterile powder for injection could be produced.

The pharmaceutical preparations made from the above-mentioned 20(R)-ginsenoside Rg3 pharmaceutical solid or liquid composition have the inhibitory activities to the tumor growth and metastasis, and the efficacy potentiation and toxicity attenuation activities when combined with the chemical or radiation therapy of tumor, and can enhance human immune functions, improve human memory, and resist the fatigue, and have detumescence, pain relieving and wound healing effects.

Compared with current technology, present invention boast of the following advantages:

1) From 20(R)-ginsenoside Rg3 pharmaceutical composition solution in the present invention, powder which is without residual organic solvent and can be completely dissolved in water can be obtained after drying; therefore, lyophilized powder for injection made from this powder can meet the specifications of the injectable preparation in "Pharmacopoeia of People's Republic of China." And different kinds of oral or external application preparations can be produced as well.

2) The injectable preparations or oral preparations made from 20(R)-ginsenoside Rg3 pharmaceutical composition in present invention have significantly improved the bioavailability, compared with current commercial oral preparations (Trade name, ShenYi Capsule). After injection, the ginsenoside Rg3 injectable preparation can completely enter into blood of human and animals, with an absolute bioavailability of 100%, which exceeds the bioavailability of current oral preparations for 20~50 folds. The oral preparations of ginsenoside Rg3 exceeds the bioavailability of current oral preparations for over 10 folds.

3) The 20(R)-ginsenoside Rg3 produced in present invention can 100% transforms to solution with adjuvant. After drying process, lyophilized powder for injection could be obtained; therefore, the material utilization rate is 100%, with a cost significant lower than that for their clathrate lyophilized powder for injection.

4) The 20(R)-ginsenoside Rg3 composition oral pharmaceutical preparations produced in present invention can be reduced half of the application dosage due to improved bioavailability, with a same or better efficacy than the current capsule, which greatly decreases the treatment cost of cancer patients.

5) The 20(R)-ginsenoside Rg3 composition injectable preparations produced in present invention has high concentration distribution in the liver and gastroenteral walls of the rats and dogs, therefore, it can be used as a good treatment for digestive tract tumors and tumor metastasis.

DESCRIPTION OF THE DRAWINGS

There are 11 attached figures in present invention.

DESCRIPTION OF THE EMBODIMENTS

Example 1

Figure 1:
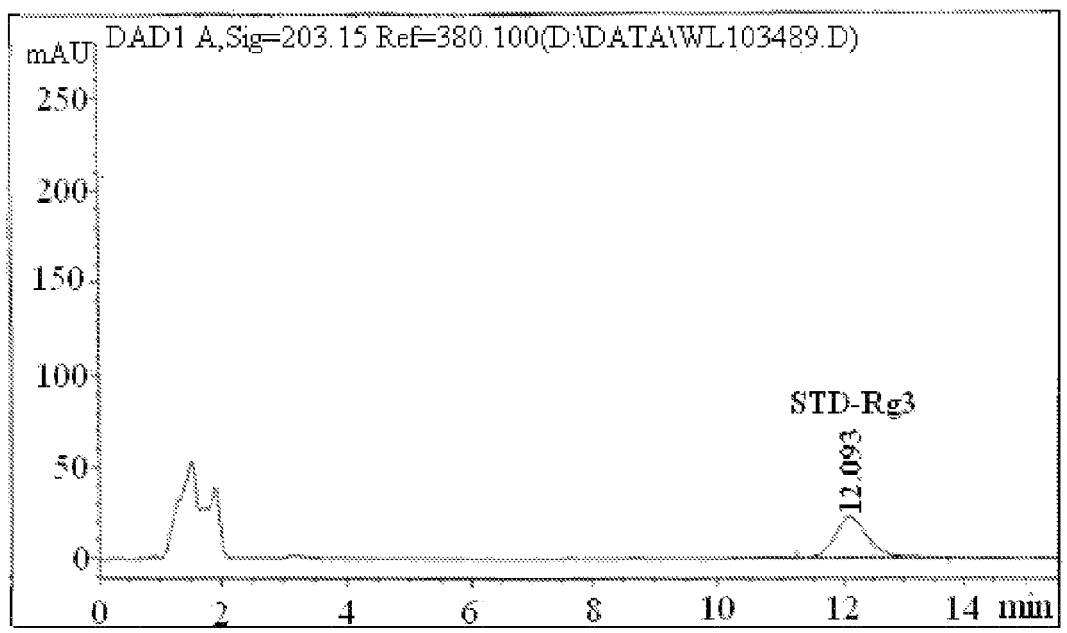
FIG. 1 is a high performance liquid chromatography determination chromatogram of the 20(R)-ginsenoside Rg3 Standard Sample.
Figure 2:
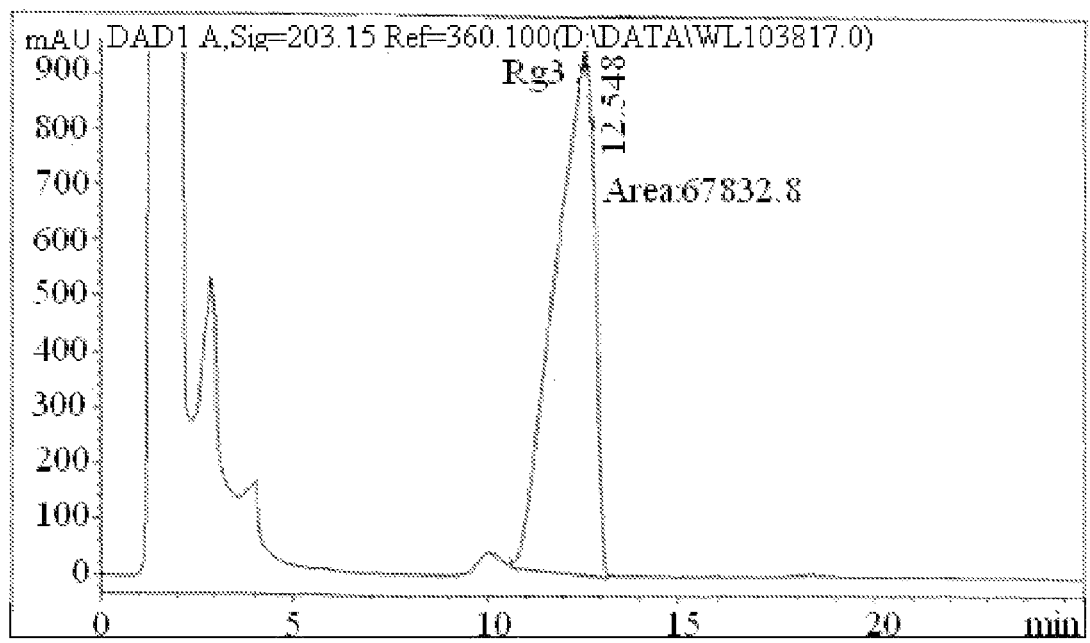
FIG. 2 is a high performance liquid chromatography chromatogram of the composition of 20(R)-ginsenoside Rg3 and deoxycholic acid sodium.

Dissolve 1 gram of 20(R)-ginsenoside Rg3 with organic solvent mixture (chloroform:ethyl acetate:ethanol:water=10:30:18:5, lower phase), and make 0.1% solution. Dissolve 100 grams of deoxycholic acid sodium in water for injection; heat the solution to 40° C., and make 30% aqueous solution. Add the prepared ginsenoside Rg3 solution into the above-mentioned deoxycholic acid sodium solution, and stir for 3 hours, and then a clear composition solution is obtained. After filtration, the solution is decompressed in a rotatory evaporator at 100° C. with a vacuum degree of 0.01 MPa to recycle the solvent to near dryness. After reconstituting the nearly dried material with distilled water to original volume, the solution is recycled again to near dryness. Repeat the above procedure once more to completely remove the organic solvent. Reconstitute the nearly dried material with water for injection (100 ml); the resultant aqueous solution is 100 ml of 20(R)-ginsenoside Rg3 composition with deoxycholic acid sodium. After high performance liquid chromatography determination, the content of ginsenoside Rg3 in composition solution is calculated to be 10 mg/ml, referred to FIGS. 1 and 2.

Example 2

Figure 3:
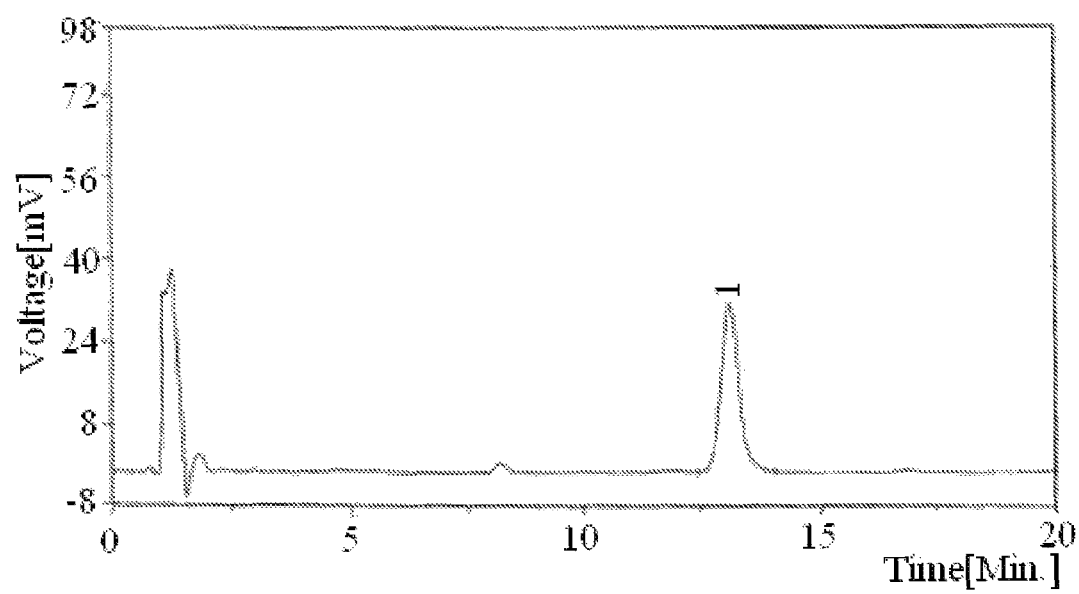
FIG. 3 is a high performance liquid chromatography chromatogram of the 20(R)-ginsenoside Rg3 Standard Sample.
Figure 4:
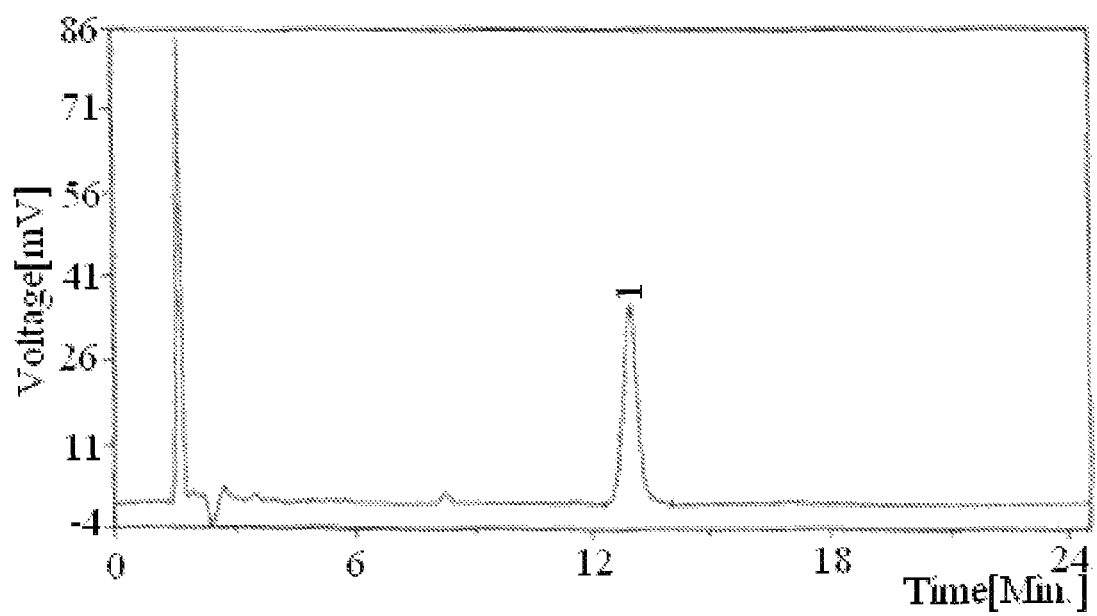
FIG. 4 is a high performance liquid chromatography chromatogram of the composition of 20(R)-ginsenoside Rg3 and sodium dodecylsulphate.

Dissolve 0.5 grams of 20(R)-ginsenoside Rg3 with organic solvent mixture (chloroform:ethyl acetate:ethanol:water=25:45:30:15, lower phase), and make 5% solution. Dissolve 100 grams of sodium dodecylsulphate in water for injection; heat the solution to 100° C., and make 0.1% aqueous solution. Add the prepared ginsenoside Rg3 solution into the above-mentioned sodium dodecylsulphate solution, and stir for 0.1 hours, and a clear composition solution is obtained. After filtration, the solution is decompressed in a rotatory evaporator at 80° C. with a vacuum degree of 0.08 MPa to recycle the solvent to a fourth of its original volume. After reconstituting the nearly dried material with distilled water to original volume, the solution is recycled again to near dryness. Repeat above mentioned procedure once more to completely remove the organic solvent. Reconstitute the nearly dried material with purified water (1000 ml); the resultant aqueous solution is 1000 ml of 20(R)-ginsenoside Rg3 composition with sodium dodecylsulphate. After high performance liquid chromatography determination, the content of ginsenoside Rg3 in composition solution is calculated to be 0.5 mg/ml, referred to FIGS. 3 and 4.

Example 3

Figure 5:
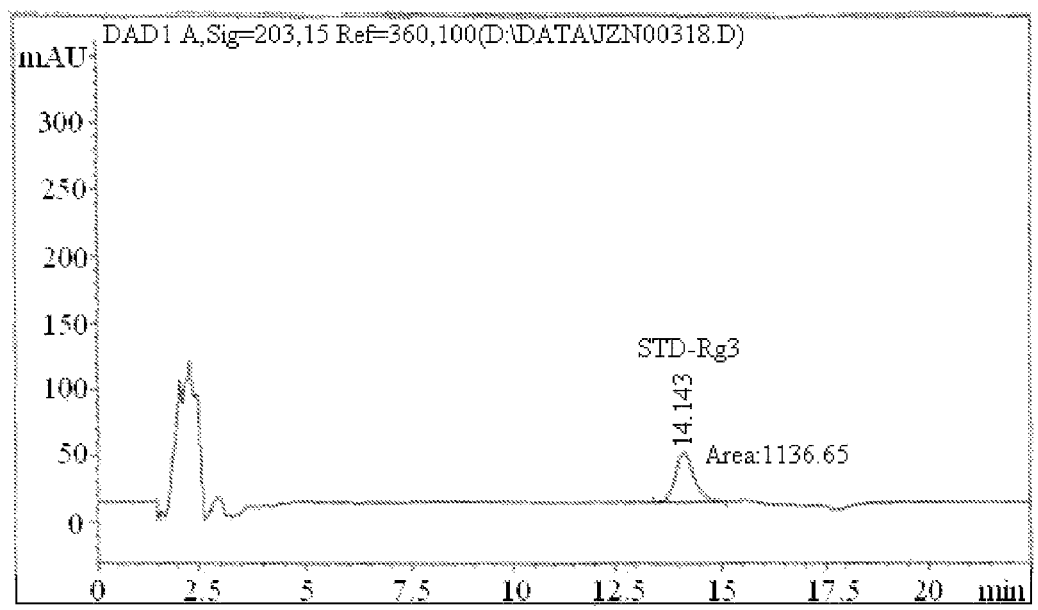
FIG. 5 is a high performance liquid chromatography chromatogram of the 20(R)-ginsenoside Rg3 Standard Sample.
Figure 6:
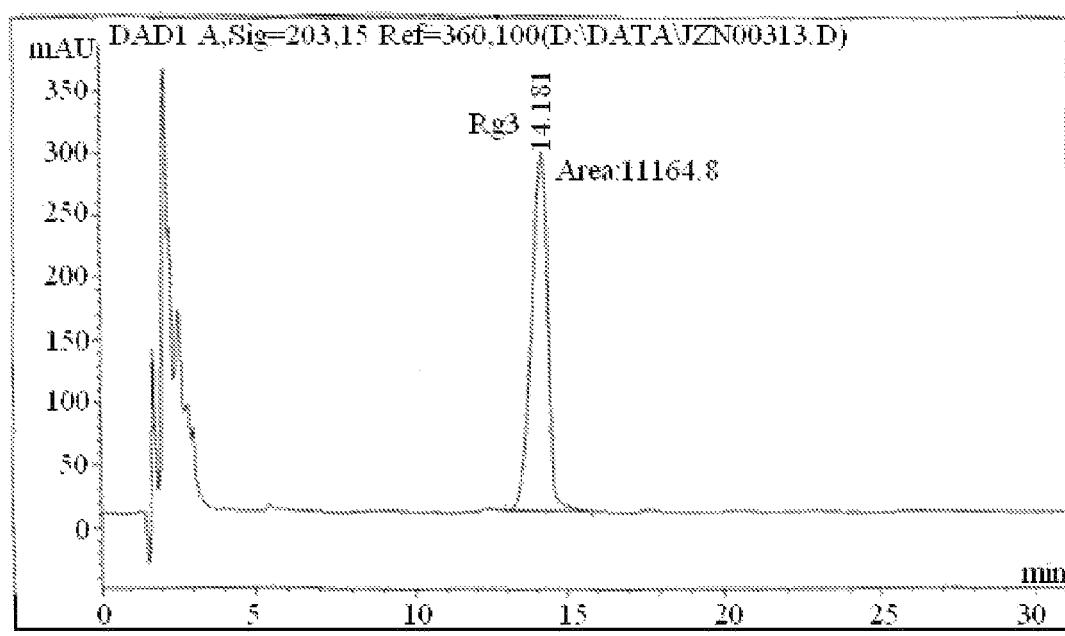
FIG. 6 is a high performance liquid chromatography chromatogram of the composition of 20(R)-ginsenoside Rg3 and 2,3,6-trihydroxypropyl-β-cyclodextrin.

Dissolve 5 grams of 20(R)-ginsenoside Rg3 with organic solvent mixture (chloroform:ethanol:water=70:30:10, lower phase), and make 0.1% solution. Dissolve 500 grams of 2,3,6-trihydroxypropyl-β-cyclodextrin in distilled water, heat the solution to 60° C., and make 20% aqueous solution. While stirring, drip the prepared ginsenoside Rg3 solution into the above-mentioned 2,3,6-trihydroxypropyl-β-cyclodextrin solution at a constant rate of 10 ml/min, and stop stirring after dripping is complete. The solution is decompressed in a rotatory evaporator at 100° C. with a vacuum degree of 0.05 MPa to recycle the solution to near dryness. After reconstituting the nearly dried material with distilled water to original volume, the solution is recycled again to near dryness. Repeat the above procedure once more. Reconstitute the concentrated material with 2.5 liters of water for injection, and the resultant aqueous solution is 20(R)-ginsenoside Rg3 water-soluble intermediate. After high performance liquid chromatography determination, the content of ginsenoside Rg3 water-soluble intermediate is calculated to be 2 mg/ml, referred to FIGS. 5 and 6.

Example 4

Figure 7:
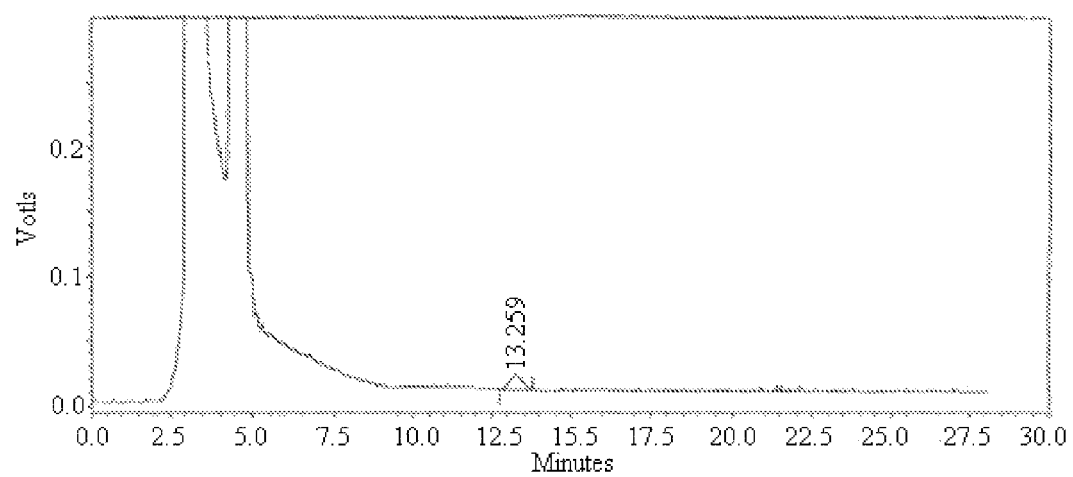
FIG. 7 is a high performance liquid chromatography chromatogram of the 20(R)-ginsenoside Rg3 Standard Sample.
Figure 8:
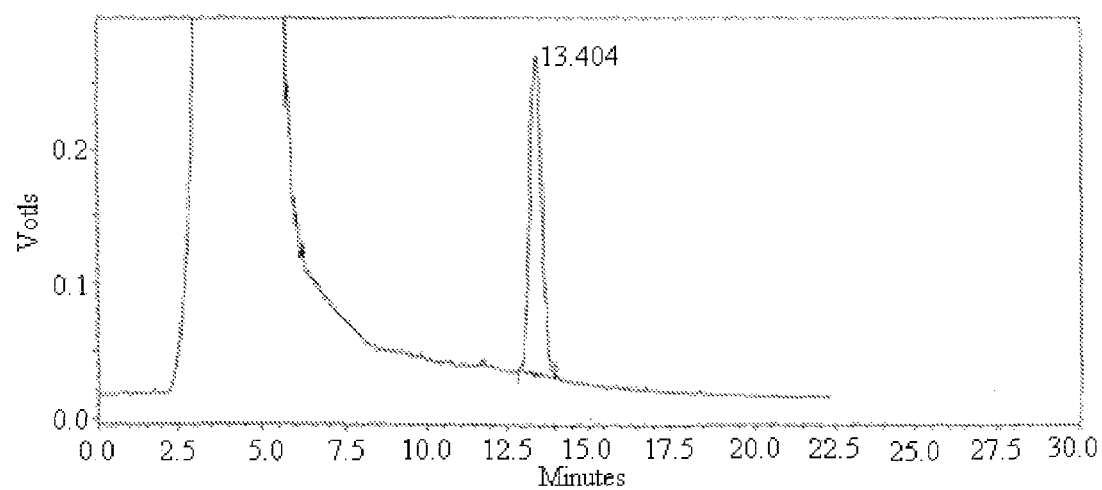
FIG. 8 is a high performance liquid chromatography chromatogram of the composition of 20(R)-ginsenoside Rg3 and β-cyclodextrin.

Dissolve 2 grams of 20(R)-ginsenoside Rg3 with organic solvent mixture (chloroform:ethanol:water=70:30:10, lower phase), and make 5% solution. Dissolve 600 grams of β-cyclodextrin in distilled water, heat the solution to 40° C., and make 30% aqueous solution. While stirring, drip the prepared ginsenoside Rg3 solution into the above-mentioned β-cyclodextrin solution at a constant rate of 5 ml/min, and stop stirring after dripping is complete. The solution is decompressed in a rotatory evaporator at a vacuum degree of 0.04 MPa to recycle the solvent to near dryness. After reconstituting the nearly dried material with distilled water to original volume, the solution is recycled again to near dryness. Repeat the above-mentioned procedure once more. Reconstitute the concentrated material with 20 liters of water for injection; the resultant aqueous solution is 20(R)-ginsenoside Rg3 water-soluble intermediate. After high performance liquid chromatography determination, the content of ginsenoside Rg3 water-soluble intermediate is calculated to be 0.1 mg/ml, referred to FIGS. 7 and 8.

Example 5-43

| Example | Main Material (g) | Organic solvent mixture used to dissolve the main material (ml) | Adjuvant (g) | Adjuvant Solution Concentration (%) | Reaction Temperature to facilitate Dissolution (C.) | Stirring Time (hour) | Composition Solution Main material:adjuvant | Rg3 (mg/ml) |
|---|---|---|---|---|---|---|---|---|
| 5 | 0.2 | Chloroform:ethyl acetate:methanol:water = 25:45:30:15, lower phase, 80 | Sodium deoxycholic acid 0.2 | 0.1 | 40 | 0.1 | 1:1 | 0.5 |
| 6 | 1 | Chloroform:ethyl acetate:methanol:water = 25:45:30:15, lower phase, 800 | Deoxycholic acid 100 | 10 | 60 | 3 | 1:100 | 10 |
| 7 | 1 | Chloroform:ethyl acetate:methanol:water = 25:45:30:15, lower phase, 800 | Deoxycholic acid 50 | 30 | 60 | 0.5 | 1:100 | 10 |
| 8 | 1 | Ethanol:water = 90:10, 1000 | Sodium dodecylsulphate 5 | 5 | 50 | 2 | 1:5 | 5 |
| 9 | 10 | Acetonitrile:methanol = 70:30, 1000 | Sodium dodecylsulphate 400 | 20 | 55 | 3 | 1:40 | 2 |
| 10 | 5 | Acetonitrile:methanol = 80:20, 500 | Sodium dodecylsulphate 100 | 10 | 45 | 1.5 | 1:20 | 1 |
| 11 | 1 | Dimethyl sulfoxide:water = 90:10, 50 | Arginine 100 | 20 | 50 | 1 | 1:100 | 2 |
| 12 | 5 | Dimethyl sulfoxide:water = 80:20, 250 | Arginine 100 | 25 | 50 | 1 | 1:20 | 1 |
| 13 | 5 | Chloroform:methanol:water = 70:30:10, lower phase, 5000 | Polymerized cyclodextrin nanoscale microparticle 500 | 30 | 100 | 5 | 1:100 | 1 |
| 14 | 2 | Chloroform:methanol:water = 60:40:10, lower phase, 200 | Polymerized cyclodextrin nanoscale microparticle 200 | 10 | 80 | 2 | 1:100 | 2 |
| 15 | 1 | Ethanol:water = 95:5, 500 | Polymerized cyclodextrin 100 | 20 | 65 | 2.3 | 1:100 | 0.5 |
| 16 | 1 | Ethanol:water = 90:10, 600 | Polymerized cyclodextrin 150 | 30 | 85 | 2.6 | 1:150 | 0.8 |
| 17 | 0.5 | Methanol:water = 90:10, 250 | Side chained cyclodextrin 200 | 10 | 100 | 1 | 1:200 | 0.5 |
| 18 | 0.5 | Methanol:water = 85:15, 200 | Side chained cyclodextrin 300 | 15 | 95 | 0.8 | 1:300 | 0.9 |
| 19 | 1 | Acetonitrile:water = 40:60, 500 | β-cyclodextrin 150 | 30 | 65 | 1.3 | 1:150 | 1 |
| 20 | 300 | Dimethyl sulfoxide:water = 90:10, 1000 | 2,6-dimethyl-β-cyclodextrin 3000 | 30 | 100 | 3 | 1:10 | 1 |
| 21 | 5 | Dimethyl sulfoxide:water = 80:20, 125 | 2,6-dimethyl-β-cyclodextrin 800 | 25 | 95 | 3 | 1:160 | 2 |
| 22 | 1 | Acetonitrile:methanol = 70:30, 200 | Nano-based β-cyclodextrin, 90 | 0.5 | 60 | 0.7 | 1:90 | 0.5 |
| 23 | 3 | Acetonitrile:methanol = 80:20, 3000 | Nano-based β-cyclodextrin, 150 | 30 | 60 | 3 | 1:50 | 2 |
| 24 | 2 | Acetonitrile:ethanol = 70:30, 200 | Sulfobutyl ether β-cyclodextrin, 140 | 25 | 75 | 1 | 1:70 | 0.5 |
| 25 | 2 | Acetonitrile:ethanol = 80:20, 400 | Sulfobutyl ether β-cyclodextrin, 180 | 15 | 95 | 3 | 1:90 | 1 |
| 26 | 1 | Propylene glycol:ethanol:Tween 80:water = 40:10:1:49, 600 | Methylated β-cyclodextrin 300 | 30 | 60 | 2 | 1:300 | 0.5 |
| 27 | 1 | Propylene glycol:ethanol:Tween 80:water = 50:20:1:29, 40 | Methylated β-cyclodextrin 150 | 25 | 65 | 1.2 | 1:150 | 1 |
| 28 | 1 | Propylene glycol:methanol:Tween 80:water = 40:10:1:49, 50 | Methyl-β-cyclodextrin, non-localized; 240 | 20 | 100 | 2.5 | 1:240 | 0.5 |
| 29 | 1 | Propylene glycol:methanol:Tween 80:water = 50:20:1:29, 65 | Methyl-β-cyclodextrin, non-localized; 300 | 30 | 95 | 1.2 | 1:300 | 0.8 |
| 30 | 2 | Dichloromethane:methanol:water = 65:35:10, lower phase, 200 | 2-hydroxypropyl-β-cyclodextrin 200 | 40 | 60 | 1.3 | 1:100 | 2 |

-continued

| Example | Main Material (g) | Organic solvent mixture used to dissolve the main material (ml) | Adjuvant (g) | Adjuvant Solution Concentration (%) | Reaction Temperature to facilitate Dissolution (C.) | Stirring Time (hour) | Composition Solution Main material:adjuvant | Rg3 (mg/ml) |
|---|---|---|---|---|---|---|---|---|
| 31 | 2 | Dichloromethane:methanol:water = 60:40:10, lower phase, 350 | 2-hydroxypropyl-β-cyclodextrin 600 | 60 | 65 | 4.8 | 1:300 | 0.1 |
| 32 | 1 | Dichloromethane:ethanol:water = 65:35:10, lower phase, 300 | 3-hydro xypropyl-β-cyclodextrin 120 | 65 | 70 | 0.9 | 1:120 | 2 |
| 33 | 1 | Dichloromethane:ethanol:water = 60:40:10, lower phase, 500 | 3-hydro xypropyl-β-cyclodextrin 300 | 65 | 80 | 1.3 | 1:300 | 0.8 |
| 34 | 2 | Chloroform:ethanol:water = 70:30:10, lower phase, 350 | 2,3-dihydroxypropyl-β-cyclodextrin 200 | 50 | 60 | 1.5 | 1:100 | 1.5 |
| 35 | 2 | Chloroform:ethanol:water = 60:40:10, lower phase, 250 | 2,3-dihydroxypropyl-β-cyclodextrin 400 | 50 | 70 | 2 | 1:200 | 0.6 |
| 36 | 5 | Dimethyl sulfoxide:methanol = 80:20, 25 | 2,3,6-trihydroxypropyl-β-cyclodextrin 500 | 65 | 65 | 1.7 | 1:100 | 0.1 |
| 37 | 0.5 | Dimethyl sulfoxide:ethanol = 90:10, 30 | Hydroxyethyl-β-cyclodextrin 75 | 30 | 80 | 0.45 | 1:150 | 0.5 |
| 38 | 0.5 | Dimethyl sulfoxide:ethanol = 80:20, 400 | Hydroxyethyl-β-cyclodextrin 175 | 60 | 85 | 0.5 | 1:350 | 0.2 |
| 39 | 1 | Chloroform:ethyl acetate:methanol:water = 25:45:30:15, lower phase, 500 | β-cyclodextrin:2-hydroxypropyl-β-cyclodextrin (1:1)mixture 150 | 25 | 60 | 1.7 | 1:150 | 2 |
| 40 | 1 | Chloroform:methanol:water = 70:30:10, lower phase, 330 | 2-hydroxypropyl-β-cyclodextrin:3-hydroxypropyl-β-cyclodextrin (1:5) mixture 400 | 20 | 70 | 2.6 | 1:400 | 1 |
| 41 | 1 | Acetonitrile:ethanol = 70:30, 100 | Polymerized cyclodextrin nanoscale microparticle:β-cyclodextrin mixture:sulfobutyl ether β-cyclodextrin (1:1:1) mixture 90 | 50 | 95 | 1.4 | 1:90 | 0.5 |
| 42 | 2 | Dimethyl sulfoxide:methanol = 80:20, 100 | 2-hydroxypropyl-β-cyclodextrin:3-hydroxypropyl-β-cyclodextrin:2,3,6-trihydroxypropyl-β-cyclodextrin (1:5:10) mixture, 480 | 60 | 80 | 1.5 | 1:240 | 2 |
| 43 | 0.5 | Propylene glycol:ethanol:Tween 80:water = 40:10:1:49, 200 | B-cyclodextrin:polymerized cyclodextrin:2-hydroxypropyl-β-cyclodextrin (2:5:5) mixture, 200 | 45 | 85 | 1.1 | 1:400 | 2 |

Example 44

Take 100 ml of 20(R)-ginsenoside Rg3 composition solution obtained from Operation Example 1, add water for injection to 1000 ml, and add 0.1 grams of injection grade active carbon and mix to uniformity. Leave it at 80° C. for 30 minutes, remove the pyrogen with 0.45 µm micropore membrane filtering, sterilize with a 0.22 µm micropore filter membrane under sterile conditions, dispense into a 10 ml sterile antibiotics tube vial under sterile conditions, and the quantity of each tube vial is 4.5~4.9 ml:5 mg. After the dispensed, the antibiotics tube vials are half-corked, they are transferred onto the plate of lyophilizer (LYO-5, manufactured in Shanghai). Close the door of the lyophilizer, turn on the lyophilizer and first freeze to below −40° C. and keep for 4 hours, and then start vacuum drying as following program for sublimation: −45~−30° C. for 4 hours, −30~−20° C. for 4 hours, −20~−15° C. for 2 hours. Finally, dry for 4 hours at 15~30° C., and the lyophilization process is complete. After lyophilization, the corks are fully plugged and aluminum covers are pressed on with a sealing machine. Sample some sample for testing. Pack the qualified tube vials. 1000 tube vials of lyophilized powder for injection (3.1 mg Rg3/vial) are obtained. The above-mentioned procedures can be carried out for Example 2-40 to produce water-soluble powder of ginsenoside Rg3.

Example 45

Take 50 liters of 20(R)-ginsenoside Rg3 composition solution obtained from Operation Example 20, place onto the stainless steel drying plate of a dual cones gyration vacuum dryer (Model SZG-4500, manufactured in Changzhou) for vacuum drying for 12 hours at 80° C. with a vacuum degree of 1.3 Pa, and obtain water-soluble powder; or, place the above-mentioned composition solution into a fluidized bed desiccator of a combined spraying dryer (Model SPG-105, made in Changzhou), and spurt the composition solution containing 20% of solid substance into the fluidized bed by a dual outlet jet nozzle, at 20° C. and at a spurt rate of 0.8 kg/hour. The input temperature of fluidized gas is 150° C., and the spurt volume can heat the fluidized bed to 75° C., and 55 kilograms of water-soluble powder with a diameter of 100~250 micrometers can be produced. Or, the above-mentioned water-soluble dried powder can be reconstituted again, and lyophilized with a procedure described at Example 35, and 10000 vials of lyophilized powder for injection can be obtained.

Example 46

An In-Vivo Experiment on the Improvement of the Bioavailability of 20(R)-Ginsenoside Rg3 Composition Granules Plasma concentrations of 20(R)-ginsenoside Rg3 in Beagle dogs are compared between oral administration of 20(R)-ginsenoside Rg3 composition granules and 20(R)-ginsenoside Rg3 material capsules. The study is contracted to the Laboratory of drug metabolism and pharmacokinetics, Shenyang Pharmaceutical University. The results demonstrate that plasma concentration of 20(R)-ginsenoside Rg3 in Beagle dogs orally administrated with 20(R)-ginsenoside Rg3 composition granules is 12 to 20 folds higher than that in dogs orally administered with 20(R)-ginsenoside Rg3 material capsules, suggesting that the bioavailability of ginsenoside Rg3 composition granules in animal body is much higher than that of capsules made from the ginsenoside Rg3 material.

Figure 9:
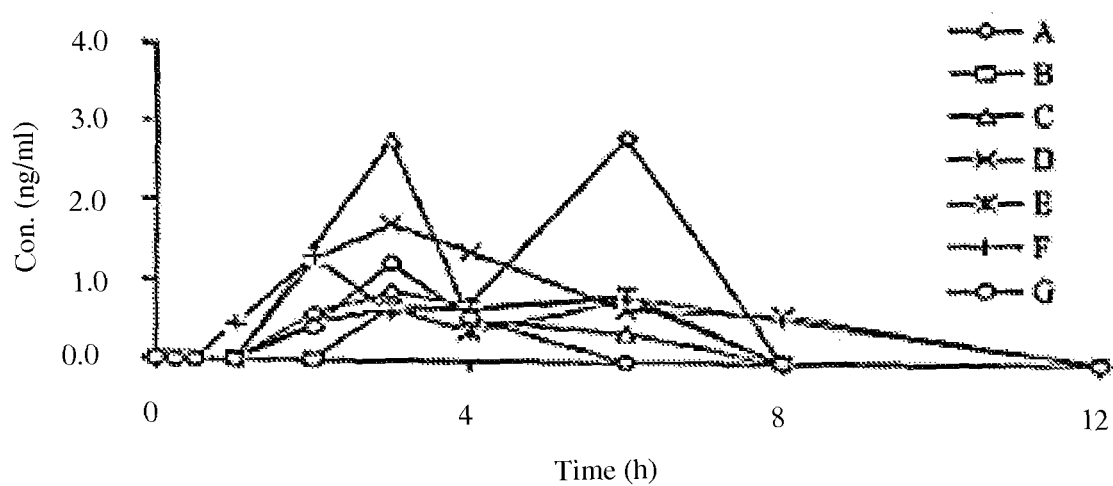
FIG. 9 is a plasma drug concentration time curve after oral administration of 5.6 grams of 20(R)-ginsenoside Rg3 granules in seven dogs.
Figure 10:
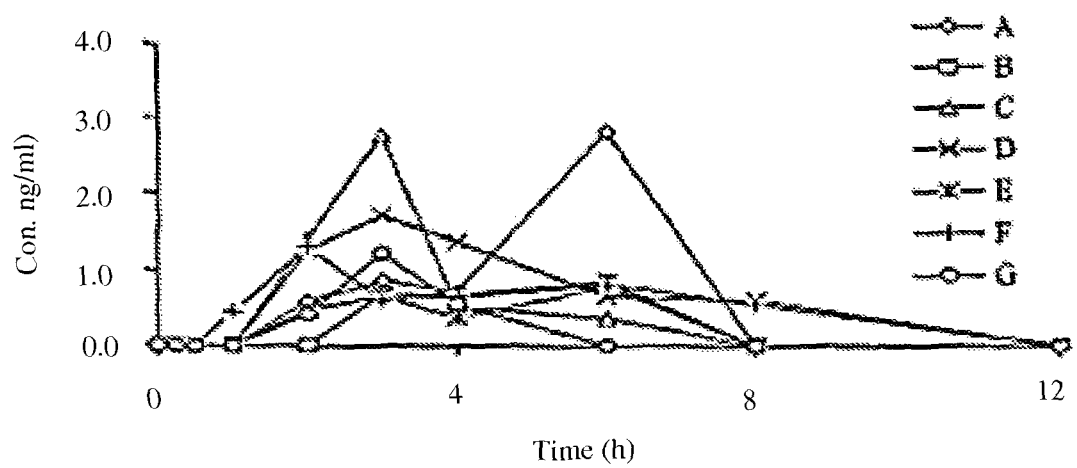
FIG. 10 is a plasma drug concentration time curve after oral administration of 3 grams of 20(R)-ginsenoside Rg3 ShenYi capsules in seven dogs.
Figure 11:
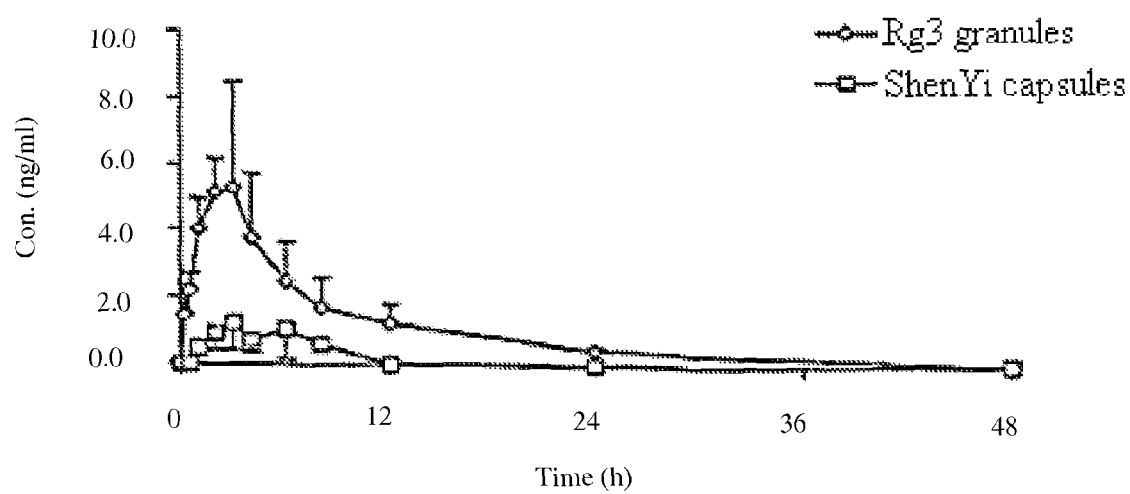
FIG. 11 is a plasma drug concentration time curve after oral administration of 20(R)-ginsenoside Rg3 granules and ShenYi capsules in seven dogs.

Beagle dogs are orally administrated with 20(R)-ginsenoside Rg3 composition granules obtained by Operation example 37, and the bioavailability is measured. The instrument used for biological samples testing is API 4000 mass spectrometer. A liquid chromatographic tandem mass spectrometric (LC/MS/MS) method is used. The plasma drug concentration time curve in seven dogs orally administrated with 5.6 grams of pharmaceutical composition of 20(R)-ginsenoside Rg3 and β-cyclodextrin (1:200, containing Rg3 30 mg) is presented in FIG. 9. The plasma drug concentration time curve in seven dogs orally administrated with 3 ShenYi capsules (containing 30 mg Rg3, 10 mg Rg3/capsule) is in FIG. 10. The mean plasma drug concentration time curves of these two treatment groups are presented in FIG. 11. Following an oral administration of the pharmaceutical composition, the maximum observed concentration ($C_{max}$) is 6.8±1.8 ng/mL at 2.3±0.9 h ($t_{max}$, the time for maximum observed concentration). The terminal half-life ($t_{1/2}$) is 6.0±0.9 h, and the area under curve (AUC0-t) is 40.0±15.7 ng·h/mL.

Example 47

The Antineoplastic Pharmacodynamic Bioassay of 20(R)-Ginsenoside Rg3 Composition Lyophilized Powder for Injection 1 Test Drug and Preparation Method Test drug: Ginsenoside Rg3 lyophilized powder for injection; batch: 20030519, specification 5 mg/vial.

Preparation method: Accurately weigh the required amount of ginsenoside Rg3 lyophilized powder for injection or relative adjuvant; add it into saline solution, up to the required concentration. The administration volume is 0.5 ml/mouse.

2 Experimental Materials 2.1 Solvent:

saline solution 2.2 Positive Controls:

Cyclophosphamide for injection (CTX), produced by Shanghai Hualian Pharmaceutical Group. Intravenous injection once daily, continued for 7 days. 5-Fluorodeoxyuridine (5Fu) for injection, produced by Shanghai Xudong Haipu Pharmaceutical Corporation, Ltd. Mitomycin C (MMC) for injection, produced by Kyowa Hakko Kogyo Co., Ltd. (Tokyo, Japan).

2.3 Tumor Source:

Human intestine cancer LOVO model, human stomach cancer MGC model, and human liver cancer QGY model, all tumor strains are in vivo subcultured for more than $2^{nd}$ generation. Mouse melanoma $B_{16}$ cell are subcultured and maintained by Pharmacology Department of Shanghai Institute of Pharmaceutical Industry.

3 Experimental Animals 3.1 Source:

Nude mice are supplied by Shanghai Laboratory Animal Center of the Chinese Academy of Sciences; the qualification certificate No. is SCXK2003-0003. $C_{57}BL/6$ and Kunming mice are supplied by Laboratory Animal Group of Shanghai Institute of Pharmaceutical Industry. The Laboratory Animal Usage License No. is SYXK (Shanghai) 2004-0015.

3.2 Body Weight

Nude mice: 6 weeks; $C_{57}BL/6$ and Kunming mice: 18~22 grams.

3.3 Sex:

Both female and male animals are used, for each test, the same gender of animals are used.

3.4 Animal Number:

For the treatment and positive control groups, 6 nude mice and 8-10 other mice are used per each group, for negative controls, 2 groups of animals are used.

4 Experimental Designs 4.1 Dosage Setup:

The administration dosage for 20(R)-ginsenoside Rg3 lyophilized powder for injection is set as 1.5, 0.75, and 0.375 mg/kg/day.

4.2 Administration Protocol:

Take intravenous administration, twice per day. For mice models inoculated with human tumor models and cells, continue injection for seven days; for mice models inoculated with mouse tumor cells, continue injection for five days.

4.3 Experimental Controls:

Negative controls: administrated with the same adjuvant as the treatment groups and the administration protocol is the same as that of the treatment groups.

Positive controls: CTX, 30 mg/kg; MMC, 2 mg/kg; 5Fu, 30 mg/kg; intraperitoneal or intravenous injection, once daily, continues for 7 days.

5 Experimental Methods 5.1 Antineoplastic Bioassay 5.1.1 Stomach In Situ Inoculation Model Take strongly growing in-vivo $2^{nd}$-generation MGC stomach cancer (cells) under sterile condition, and prepare it into a cell suspension with a density of $2 \times 10^7$ cells/ml by a homogenate method. Inject 0.05 ml of the cell suspension into the muscular layer of greater curvature of stomach of the nude mice via a surgery operation. Administrate the above mice with test drug next day according to the experimental design protocol, and calculate the life extension percentage of the tumor bearing host:

Life extension percentage (%)=(mean survival days of treatment group/mean survival days of control)× 100%

5.1.2 Liver In Situ Inoculation Model

Take strongly growing in-vivo $2^{nd}$-generation QGY tumor cells under sterile condition, and prepare it into a cell suspension with a density of about $1-2 \times 10^7$ cells/ml by a 1:6 homogenate method. The cell suspension is filtered with a 100 mesh stainless steel sieve, and reserved for further usage. After routine sterilization and anesthesia of the nude mice, incise the abdomen skin below the xiphoid of the middle of the abdominal cavity and then open the abdominal cavity. Expose the liver and inject 0.05 ml cell suspension into the liver parenchyma with an imported gauge 28½ ml syringe. After closing the abdominal cavity, suture the muscular layer and skin layer consecutively. The nude mice are housed in a laminar cubicle, and the feeder, bedding, caging, and all operation apparatus used are all sterilized by autoclaving. Administrate the test drug next day according to the experimental design protocol, record the survival time within 45 days of post dosing for each group, and calculate the life extension percentage of the tumor bearing host, compared with that of negative controls.

5.2 Antineoplastic Efficacy Potentiation Bioassay

5.2.1 Armpit Subcutaneous Inoculation Model

Take strongly growing tumor cells under sterile condition, and prepare it into a cell suspension with a density of about $1\sim2\times10^7$ cells/ml by a homogenate method. Inoculate 0.2 ml/mouse of the cell suspension subcutaneously into the armpit of the axillary host. Administrate the test drug next day according to the experimental design protocol. Euthanize each group animal after ~3 weeks and remove the tumor from mice and weigh it. Calculate the tumor inhibition percentage by the following formula:

Tumor inhibition percentage (%)=[(mean tumor weight of control group−mean tumor weight of treatment group)/mean tumor weight of control group]×100%

5.2.2 Caudal Vein Inoculation Model

Mouse B16 melanoma cells in logarithmic growth phase are taken out under sterile condition, and a cell suspension with a density of about $2.5\times10^5$ cells/ml is prepared. Inoculate 0.2 ml/mouse of cell suspension into caudal vein of $C_{57}BL/6$ mouse. Administrate the test drug next day according to the experimental design protocol, euthanize the animal after ~3 weeks and remove the lungs from mice and count the metastatic colony in the lungs of each mouse. Calculate the tumor inhibition percentage based on the group mean colony by the following formula:

Tumor inhibition percentage (%)=[(mean colony of control group−mean colony of treatment group)/mean colony of control group]×100%

5.3 Antineoplastic Toxicity Attenuation Bioassay

The effects of ginsenoside Rg3 lyophilized powder for injection on the white blood cell count changes in mice induced by chemotherapy agents are evaluated. Blood sample is collected from 80 $C_{57}BL/6$ mice via ocular venous plexus, and the white cell counting for each mouse is performed by the routine blood cell counting chamber procedure. Mice with a white blood cell counting of 7500±300 are selected, and are randomly assigned into different groups, 10 mice for each group. Except for the blank control group, the animals in other groups are administrated with 100 mg/kg CTX ip ×2 at Day 0 and 2. Administrate the test drug according to the above-mentioned protocol, count the white blood cell starting at day 0, and then count for every 3 day during experimental period. Measure each group mice white blood cell count and calculate the mean white cell count and their standard deviations for each group in each time (date) point, until the white blood cell count of positive controls recovers to normal.

5.4 Immunological Bioassay

5.4.1 NK Cell Activity Bioassay in Lewis Lung Cancer Cell Bearing $C_{57}BL/6$ Mice Cell suspension of Lewis lung cancer is prepared under sterile condition and 0.05 ml (about $1\times10^6$ tumor cells) of this suspension is subcutaneously inoculated into the digiti pedis of $C_{57}BL/6$ mice. The mice are randomly assigned next day into different groups, and administrated the test drug according to the experimental design protocol. On the next day of last dosing, the spleens are taken out of mice under sterile condition, and spleen cell suspension is prepared with a 100 mesh sieve. The erythrocytes are removed by hypotonic treatment, and the resultant cell suspension is transferred into cell culture flask. After incubated in 37° C., 5% $CO_2$ for 1 hour, the attached cells are removed, and cells are counted and adjusted to a density of $3\times10^6$/ml, and used as effector cell. The target cells are prepared by routinely culturing $L_{929}$ in-vitro cells for 24 hours, and adjusting the cell concentration to $1.5\times10^5$/ml, and the ratio of effector to target is 20:1. The effector cell and target cell are consecutively added into 96 well cell culture plates, making the controls of effector cell and target cell as well, and cultured for 4 hours at 37° C., 5% $CO_2$. The MTT stain solution is added and the cells are further cultured for 2 hours, after then, the digestion solution is added, and the OD value for each well are measured next morning. The NK cell activities are calculated by the following formula:

NK cell activities (%)={[mean OD of target control−(mean OD of experiment group−mean OD of effector cell)]/mean OD of target control}×100%.

5.4.2 Abdominal Cavity Macrophage Phagocytosis of Normal Kunming Mice

The male Kunming mice are randomly assigned into different groups, and administrated the test drug according to the experimental design protocol. After last dosing, 1.5 ml of 0.5% aminopeptodrate is intraperitoneally injected into each mouse. After 24 hours, 0.2 ml of $1\times10^6$/ml chicken red blood cell suspension is intraperitoneally injected into each mouse. Forty minutes after the injection, the intraperitoneal fluid is eluted with saline solution and collected, and then centrifuged. The precipitated pellets following centrifugation is smeared onto a slide. After methanol fixation, Giemsa staining, and mounting of the slides, the macrophages number which have engulfed the chicken red blood cells are counted from 100 macrophages for each mouse under an oil-immersion microscope, and the total number of chicken red blood cells engulfed is counted too. The phagocytosis percentage and phagocytosis indices are calculated by the following formula:

Phagocytosis percentage=(number of macrophages engulfing the chicken red blood cells in 100 macrophages/100 macrophages)×100%;

Phagocytosis indices=total number of macrophages chicken red blood cells engulfed in 100 macrophages/100 macrophages.

5.4.3 IL-2 Activity Bioassay in Lewis Lung Cancer Cell Bearing $C_{57}BL/6$ Mice The double antibodies sandwich ELISA method is used. Coat the anti mice IL-2 monoclonal antibody over an ELISA plate, and IL-2 in the samples or standards are bound with the monoclonal antibody, and the free unbounded components are washed out. Meanwhile, biotinylated anti mice IL-2 antibody and horseradish peroxidase labeled avidin are added, and the biotin and the avidin are specifically bound. Anti mice IL-2 antibody is bound with IL-2 which is bound in the monoclonal antibody, and an immunocomplex is formed. The free components are washed out. After coloration reagents are added, the color has changed into blue, and the termination solution is added again, and the color has changed into yellow. The OD of the solution s measured at 450 nm, and the IL-2 concentration is in proportion with $OD_{450}$. By the calibration curve, the concentrations of IL-2 in the samples could be obtained.

6 Experimental Results 6.1 For the comparison results of antineoplastic efficacy bioassay to the liver cancer of ginsenoside Rg3 lyophilized powder for injection and Rg3 capsules, refer to Table 1 and Table 2.

6.2 For the results of antineoplastic efficacy bioassay to intestine cancer and gastric cancer of ginsenoside Rg3 lyophilized powder for injection, refer to Table 3 and Table 4.

6.3 For the results of chemotherapy efficacy potentiation bioassay of ginsenoside Rg3 lyophilized powder for injection, refer to Table 5.

6.4 For the results of chemotherapy toxicity attenuation bioassay of ginsenoside Rg3 lyophilized powder for injection, refer to Table 6.

6.5 For the results of immune function enhancement bioassay of ginsenoside Rg3 lyophilized powder for injection, refer to Table 7 to Table 9.

TABLE 1

The Comparative Efficacy Bioassay between Ginsenoside Rg3 Lyophilized Powder for Injection and Capsules on Human Liver Cancer QGY Model (N = 3)

| Sample | Dosage mg/kg/d | Dosing Protocol | Total Dosage (mg) | Animal Number (initiation/end) | Body Weight of Animals(g) Initiation | Mean Survival Time (d) mean ± SD | Life Extension Percentage T/C × % |
|---|---|---|---|---|---|---|---|
| Rg3 powder injection preparation | 1.5 | iv × 14 bid | 42 | 6/0 | 22.3 | 29.60 ± 2.4*** | 135.16 |
| Rg3 powder injection preparation | 0.75 | iv × 14 bid | 21 | 6/0 | 21.7 | 28.50 ± 3.3*** | 130.14 |
| Rg3 capsules | 3.0 | ig × 14 qd | 84 | 6/0 | 22.0 | 28.80 ± 2.8*** | 131.51 |
| CTX | 30 | ip × 7 qd | 210 | 6/0 | 21.7 | 34.50 ± 4.0*** | 157.53 |
| Negative Control | Relative adjuvant | iv × 14 bid | 84 | 12/0 | 21.8 | 21.90 ± 2.35 | |

***Compared with negative control group, p < 0.01. Life prolong rate > 125% counted on antineoplastic effective;
The trade name of capsules is ShenYi capsule.

TABLE 2

The Comparative Lung Antimetastatic Efficacy Bioassay between Ginsenoside Rg3 Lyophilized Powder for Injection and Capsules on Mouse Melanoma B16 Model (N = 3)

| Sample | Dosage mg/kg/d | Dosing Protocol | Total Dosage (mg) | Animal Number Initiation/end | Body Weight of Animals(g) Initiation/end | Lung Colony (number) mean ± SD | Antimetastatic Percentage % |
|---|---|---|---|---|---|---|---|
| Rg3 powder injection preparation | 1.5 | iv × 14 bid | 42 | 10/10 | 20.1/24.7 | 20.6 ± 6.8*** | 55.33 |
| Rg3 powder injection preparation | 0.3 | iv × 14 bid | 8.4 | 10/10 | 19.8/25.3 | 26.5 ± 6.1*** | 42.54 |
| Rg3 for capsules | 6 | ig × 10 qd | 60 | 10/10 | 19.8/24.8 | 22.8 ± 6.7*** | 50.56 |
| Rg3 for capsules | 3 | ig × 10 qd | 30 | 10/10 | 19.9/25.2 | 27.5 ± 7.7*** | 40.37 |
| CTX | 100 | ip × 2 qd | 200 | 10/10 | 19.8/22.6 | 3.5 ± 3.7*** | 92.41 |
| Negative Control | Relative adjuvant | iv × 14 bid | 42 | 20/20 | 19.7/25.3 | 46.12 ± 12.46 | — |

***Compared with negative controls, p < 0.001, as same as following table.

TABLE 3

The Efficacy Bioassay of Ginsenoside Rg3 Lyophilized Powder for Injection on Human Intestine Cancer LOVO Model (N = 3)

| Sample | Dosage mg/kg/d | Dosing Protocol | Animal Number (initiation/end) | Body Weight of Animals (g) Initiation | Mean Survival Time (d) mean ± SD | Life Extension Percentage T/C × % |
|---|---|---|---|---|---|---|
| Rg3 powder injection preparation | 3.0 | iv × 14 bid | 6/0 | 21.5 | 21.88 ± 5.8*** | 160.88 |
| Rg3 powder injection preparation | 1.5 | iv × 14 bid | 6/0 | 22.7 | 21.72 ± 3.1*** | 159.71 |
| Rg3 powder injection preparation | 0.75 | iv × 14 bid | 6/0 | 22.4 | 20.30 ± 4.7*** | 149.26 |
| Rg3 powder injection preparation | 0.375 | iv × 14 bid | 6/0 | 21.9 | 17.95 ± 3.5*** | 131.98 |
| CTX | 30 | ip × 7 qd | 6/1 | 22.2 | 29.20 ± 4.8*** | 214.71 |
| Negative Control | Relative adjuvant | iv × 14 bid | 12/12 | 21.1 | 13.60 ± 2.39 | — |

TABLE 4

The Efficacy Bioassay of Ginsenoside Rg3 Lyophilized Powder for Injection on Human Gastric Cancer MGC Model (In Situ Inoculation, N = 3)

| Sample | Dosage mg/kg/d | Dosing Protocol | Animal Number (initiation/end) | Body Weight of Animals (g) Initiation | Mean Survival Time (d) mean ± SD | Life Extension Percentage T/C × % |
|---|---|---|---|---|---|---|
| Rg3 powder injection preparation | 3.0 | iv × 14 bid | 6/0 | 21.2 | 36.88 ± 3.0** | 162.04 |
| Rg3 powder injection preparation | 1.5 | iv × 14 bid | 6/0 | 21.1 | 35.71 ± 3.1*** | 156.90 |
| Rg3 powder injection preparation | 0.75 | iv × 14 bid | 6/0 | 20.5 | 33.15 ± 3.6*** | 145.65 |
| Rg3 powder injection preparation | 0.375 | iv × 14 bid | 6/0 | 20.4 | 29.32 ± 4.7*** | 128.82 |
| CTX | 30 | ip × 7 qd | 6/2 | 21.8 | 41.20 ± 3.8*** | 181.02 |
| Negative Control | Relative adjuvant | iv × 14 bid | 12/0 | 20.7 | 22.76 ± 2.14 | |

TABLE 5

The Efficacy Bioassay of Ginsenoside Rg3 Lyophilized Powder for Injection Combined with CTX on Mouse Melanoma B16 Model (N = 3)

| Sample | Dosage mg/kg/d | Dosing Protocol | Animal Number Initiation/End | Body Weight of Animals (g) Initiation/End | Lung Colony (number) mean ± SD | Antimetastatic Percentage % |
|---|---|---|---|---|---|---|
| Rg3 powder injection preparation | 3.0 | iv × 14 bid | 10/10 | 20.3/25.3 | 19.1 ± 7.9*** | 62.03 |
| Rg3 powder injection preparation | 1.5 | iv × 14 bid | 10/10 | 20.5/25.2 | 22.4 ± 6.9*** | 55.47 |
| Rg3 powder injection preparation | 0.75 | iv × 14 bid | 10/10 | 19.5/24.7 | 27.3 ± 8.7*** | 45.73 |
| Rg3 powder injection preparation | 0.375 | iv × 14 bid | 10/10 | 20.4/25.2 | 30.2 ± 7.3*** | 39.96 |
| Rg3 + CTX | 3.0 + 15 | iv × 14 bid + ip × 7 qd | 10/10 | 19.8/23.8 | 14.1 ± 3.6*** | 71.97 |
| Rg3 + CTX | 1.5 + 15 | iv × 14 bid + ip × 7 qd | 10/10 | 19.1/24.5 | 16.3 ± 6.1** | 67.59 |
| Rg3 + CTX | 0.75 + 15 | iv × 14 bid + ip × 7 qd | 10/10 | 19.9/24.1 | 19.2 ± 4.7*** | 61.83 |
| Rg3 + CTX | 0.375 + 15 | iv × 14 bid + ip × 7 qd | 10/10 | 19.6/24.2 | 21.9 ± 7.6*** | 56.46 |
| CTX | 15 | ip × 7 qd | 10/10 | 20.2/24.7 | 26.1 ± 5.2*** | 48.11 |
| CTX | 30 | ip × 7 qd | 10/10 | 19.9/22.6 | 3.30 ± 2.6*** | 93.44 |
| Negative Control | Relative adjuvant | iv × 14 bid | 20/20 | 20.1/25.5 | 50.3 ± 13.1 | |

TABLE 6

The Chemotherapy efficacy potentiation and Toxicity Attenuation Efficacy Bioassay of Ginsenoside Rg3 Lyophilized Powder for Injection (N = 20)

| Group | | Dosage (mg/kg/d) | Mean Tumor weight (g, mean ± SD) | Tumor Inhibition Percentage (%) | WBC ($10^9$/L) | Hb (g/L) | RBC $10^{12}$/L |
|---|---|---|---|---|---|---|---|
| $H_2O$ Control | | 1.5 × 8 | 1.84 ± 0.85 | | 6.3 ± 0.8 | 93 ± 2.5 | 3.2 ± 0.1 |
| Rg3 | | 1.5 × 8 | 0.69 ± 0.14** | 62.50 | 8.1 ± 0.2** | 109 ± 6.0** | 3.7 ± 0.4** |
| chemotherap | CTX | 10 × 3 | 0.89 ± 0.29** | 56.52 | 3.2 ± 0.5** | 82 ± 8.4** | 2.8 ± 0.3** |
| | 5Fu | 25 × 3 | 1.08 ± 0.34** | 41.30 | 3.9 ± 0.3** | 90 ± 13.0 | 3.1 ± 0.4 |
| | MTX | 5 × 3 | 0.27 ± 0.01** | 85.32 | 1.6 ± 0.1** | 51 ± 1.0** | 1.8 ± 0.1** |
| | PDD | 1 × 3 | 1.09 ± 0.30** | 40.76 | 6.0 ± 0.2 | 90 ± 6.0 | 3.1 ± 0.2 |

TABLE 6-continued

The Chemotherapy efficacy potentiation and Toxicity Attenuation Efficacy
Bioassay of Ginsenoside Rg3 Lyophilized Powder for Injection (N = 20)

| Group | Dosage (mg/kg/d) | Mean Tumor weight (g, mean ± SD) | Tumor Inhibition Percentage (%) | WBC ($10^9$/L) | Hb (g/L) | RBC $10^{12}$/L |
|---|---|---|---|---|---|---|
| Rg3 injection powder + CTX | 1.5 × 8 + 10 × 3 | 0.48 ± 0.12** | 73.91 | 7.1 ± 0.3** | 85 ± 3.6 | 2.8 ± 0.8 |
| Rg3 injection powder + 5Fu | 1.5 × 3 + 25 × 3 | 0.95 ± 0.17** | 48.37 | 7.8 ± 0.3** | 87 ± 14.0 | 2.8 ± 0.8 |
| Rg3 injection powder + MTX | 1.5 × 8 + 5 × 3 | 0.20 ± 0.04** | 89.13 | 5.2 ± 0.8* | 91 ± 10.0 | 3.1 ± 1.0 |
| Rg3 injection powder + PDD | 1.5 × 8 + 1 × 3 | 1.03 ± 0.28** | 44.02 | 6.6 ± 0.8* | 103 ± 18.0* | 3.6 ± 0.5* |

The implanted tumor in animals is mouse liver cancer model (Heps).
Compared with control group,
*p < 0.05;
**p < 0.01;
Others, p > 0.05.

TABLE 7

Effects of Ginsenoside Rg3 Lyophilized Powder for Injection
on NK Activities of Cancer Bearing Mice (N = 3)

| Group | Dosage (mg/kg) | Dosing Protocol | OD Value mean ± SD | NK activity (%) |
|---|---|---|---|---|
| Rg3 powder injection preparation | 3.00 | po × 10 qod | 0.387 | 42.29** |
| | 0.60 | po × 10 qod | 0.351 | 46.41** |
| | 0.12 | po × 10 qod | 0.368 | 43.82** |
| Total ginsenoside | 100 | po × 10 qod | 0.381 | 41.83** |
| Control | Relative adjuvant | po × 10 qd | 0.525 0.655 | 19.84 |

**p < 0.01,
OD mean value of Target cells control.

TABLE 8

Effects of Ginsenoside Rg3 Lyophilized Powder for Injection
on IL-2 Activities of Cancer Bearing Mice (N = 3)

| Group | Dosage (mg/kg) | Dosing Protocol | Animal Number | IL-2 activity/cpm mean ± SD |
|---|---|---|---|---|
| Rg3 powder injection preparation | 3.00 | po × 10 qod | 6 | 2836 ± 326** |
| | 0.60 | po × 10 qod | 6 | 3122 ± 735** |
| | 0.12 | po × 10 qod | 6 | 2414 ± 539** |
| Total ginsenoside | 100.00 | po × 10 qod | 6 | 2785 ± 255** |
| Control | Relative adjuvant | po × 10 qod | 10 | 1351 ± 127 |

**p < 0.01

TABLE 9

Effects of Ginsenoside Rg3 Lyophilized Powder for Ingection on
Abdominal Cavity Macrophage Phagocytosis of Normal Kunming Mice

| | | | Phagocytosisnsis (mean ± SD) | |
|---|---|---|---|---|
| Group | Dosage (mg/kg) | Dosing Protocol | Phagocytosis Percentage | Phagocytosis Index |
| Rg3 powder injection preparation | 3.00 | po × 10 qd | 31.80 ± 10.00** | 0.55 ± 0.11** |
| | 0.60 | po × 10 qd | 32.80 ± 10.30** | 0.58 ± 0.14** |
| | 0.12 | po × 10 qd | 28.70 ± 7.40** | 0.50 ± 0.11** |
| Total ginsenoside | 100.00 | po × 10 qd | 29.60 ± 10.00** | 0.55 ± 0.11** |
| Control | Relative adjuvant | po × 10 qd | 20.90 ± 5.80 | 0.34 ± 0.10 |

**p < 0.01

Example 48

The Antifatigue Efficacy Bioassay of
20(R)-Ginsenoside Rg3 Composition Capsules

1 Antifatigue Efficacy Bioassay of 20(R)-Ginsenoside Rg3 Composition Capsules in Mice
1.1 Materials and Methods
1.1.1 Samples:
  20(R)-ginsenoside Rg3 composition capsules in which the content is white powder, supplied by Dalian Fusheng Natural Medicine Development Corporation, Ltd. Dilute it with distilled water to the expected concentrations.
1.1.2 Experimental Animals:
  240 male grade 1 Kunming mice supplied by Laboratory Animal Center of Sichuan University, the Certificate No. is No. 67 of Sichuan Laboratory Animal Quality Administration.
1.1.3 Dosage Selection:
  Based on the proposed human dosage of 10 mg/60 kg/d, the low, mid and high dosage group are selected to be 10, 20, and 30 folds of the proposed human dosage, i.e. related to animal 1.67, 3.34, and 5.01 mg/kg/d.
1.1.4 Experimental Methods:
  The animals are assigned randomly into a negative control and 3 treatment groups, based on its body weights. The test article is administrated (2%) by a gavage, once daily. The negative controls are administrated with distilled water. The administration is continued for 30 days. After last dosing, different indicators are measured individually.
1.1.4.1 Loaded Swimming Test:
  30 minutes after last gavage, the mice are loaded with 5% body weight of lead block, and put into a swimming cabinet (depth 30 cm, water temperature 25±0.5° C.), and let swim freely. Record the retention time from starting of swimming to the death of the animal, i.e. the swimming time of mice.

1.1.4.2 Pole Climbing Test:

30 minutes after last gavage, the mice are placed on a Plexiglas pod of pole base, and kept in a static muscle tonic state. Record the retention time from climbing starting to falling from the pod because of muscle fatigue. Repeat the procedure for 3 times, and the total retention time in 3 measurements is the pole climbing time (in seconds) of mice.

1.1.4.3 Blood Urea Nitrogen and Liver Glycogen Determinations:

30 minutes after last gavage, put the mice into a swimming cabinet (depth 30 cm, water temperature 30±0.5° C.) to let them swim for 90 minutes. After then, blood samples are collected from ocular venous plexus, and the content of serum urea nitrogen (diacetyl oxime method) is determined, the liver is taken out and liver glycogen (anthrone method) are determined.

1.1.4.4 Lactic Acid Determinations:

30 minutes after last gavage, the blood samples are collected from ocular venous plexus of mice, and blood lactic acid content is determined (by SBA biosensor procedure). After then, the mice are put into a swimming cabinet (depth 30 cm, water temperature 30±0.5° C.) to swim for 10 minutes; a lead block is loaded on the tail base of the mice. And the blood samples are collected from ocular venous plexus of mice immediately after swimming start, and 30 minutes after swimming and blood lactic acid content are determined.

1.1.4.5 Statistical Analysis:

The study data are analyzed by analysis of variation, q test or rank sum test, with a SPSS 9.0 statistical software.

1.2 Results 1.2.1 Effects of 20(R)-Ginsenoside Rg3 Composition Capsules on the Body Weight of Mice From Table 1, it could be demonstrated that there are no significant differences in the body weight of mice between treatment groups and the controls, both on the middle and end period of the experiment (P>0.05).

TABLE 1

Body Weights of the Mice (Mean ± SD)

| Group | Animal number | Initiation body weight (g) | Middle term body weight (g) | End body weight (g) |
| --- | --- | --- | --- | --- |
| Negative Control | 57 | 20.58 ± 1.51 | 30.04 ± 3.44 | 34.04 ± 4.21 |
| Low | 59 | 20.61 ± 1.43 | 28.34 ± 2.95 | 33.08 ± 3.88 |
| Mid | 58 | 20.71 ± 1.41 | 29.90 ± 3.12 | 32.83 ± 3.65 |
| High | 58 | 20.62 ± 1.48 | 28.36 ± 2.77 | 32.34 ± 3.29 |

1.2.2 Effects of 20(R)-Ginsenoside Rg3 Composition Capsules on Loaded Swimming Time of Mice From Table 2, it could be demonstrated that loaded swimming time of high and low dose group mice are significantly increased (P<0.05), compared with controls; and there are no significant difference between the mid dose group and negative control (P>0.05).

TABLE 2

Loaded Swimming Time of Mice (Mean ± SD)

| Group | Animal number | Swimming time (second) | P value* |
| --- | --- | --- | --- |
| Negative Control | 14 | 387 ± 239 | |
| Low | 14 | 703 ± 597 | <0.05 |
| Mid | 14 | 519 ± 167 | >0.05 |
| High | 14 | 707 ± 430 | <0.05 |

*Compared with negative control.

1.2.3 Effects of 20(R)-Ginsenoside Rg3 Composition Capsules on Pole Climbing Time of Mice From Table 3, it could be demonstrated that pole climbing time of mid and low dose group mice are significantly increased (P<0.05), compared with controls; and there are no significant differences between the high dose group and negative control (P>0.05).

TABLE 3

Pole Climbing Time of Mice (Mean ± SD)

| Group | Animal number | Swimming time (second) | P value* |
| --- | --- | --- | --- |
| Negative Control | 13 | 172 ± 115 | |
| Low | 13 | 340 ± 153 | <0.05 |
| Mid | 13 | 332 ± 337 | <0.05 |
| High | 13 | 183 ± 84 | >0.05 |

*Compared with negative control.

1.2.4 Effects of 20(R)-Ginsenoside Rg3 Composition Capsules on Post Sport Serum Urea Nitrogen Level of Mice From Table 4, it could be demonstrated that post sporting serum urea nitrogen level of high and mid dose group mice are significantly decreased (P<0.05), compared with controls; and there are no significant differences between the low dose group and negative control (P>0.05).

TABLE 4

Post Sporting Serum Urea Nitrogen Level of Mice (Mean ± SD)

| Group | Animal number | Serum urea nitrogen level (mg/dl) | P value* |
| --- | --- | --- | --- |
| Negative Control | 12 | 27.95 ± 3.32 | |
| Low | 12 | 26.66 ± 4.24 | >0.05 |
| Mid | 12 | 24.89 ± 3.70 | <0.05 |
| High | 12 | 22.92 ± 2.25 | <0.05 |

*Compared with negative control.

1.2.5 Effects of 20(R)-Ginsenoside Rg3 Composition Capsules on Post Sporting Liver Glycogen Level of Mice From Table 5, it could be demonstrated that post sporting liver glycogen level of high dose group mice are significantly increased (P<0.05), compared with controls; and there are no significant differences between the low and mid dose group and negative control (P>0.05).

TABLE 5

Post Sporting Liver Glycogen Level of Mice (Mean ± SD)

| Group | Animal number | Liver glycogen level (mg/dl) | P value* |
|---|---|---|---|
| Negative Control | 15 | 1817.07 ± 1076.76 | |
| Low | 14 | 2327.14 ± 1075.33 | >0.05 |
| Mid | 15 | 1942.53 ± 761.87 | >0.05 |
| High | 14 | 2611.78 ± 1049.64 | <0.05 |

*Compared with negative control.

1.2.6 Effects of 20(R)-Ginsenoside Rg3 Composition Capsules on Blood Lactic Acid Level Post Sporting From Table 6 and 7, it could be demonstrated that either for the accumulation of blood lactic acid during the sporting or for the elimination blood lactic acid post sporting, there are no significant differences between the low, mid and high dose group and negative control (P>0.05).

TABLE 6

Blood Lactic Acid Accumulation during Sporting Of Mice (Mean ± SD)

| | | Blood lactic acid level (mmol/L) | | | |
|---|---|---|---|---|---|
| Group | Animal number | Pre-sporting (A) | Post sporting 0 minutes (B) | Difference (B − A) | P value* |
| Negative Control | 10 | 2.70 ± 1.50 | 5.25 ± 1.22 | 2.56 ± 1.90 | |
| Low | 13 | 3.23 ± 1.20 | 5.68 ± 1.42 | 2.45 ± 1.57 | >0.05 |
| Mid | 14 | 2.90 ± 1.01 | 5.15 ± 1.14 | 2.25 ± 1.12 | >0.05 |
| High | 13 | 2.91 ± 0.82 | 5.60 ± 1.43 | 2.69 ± 1.49 | >0.05 |

*Difference (B − A), compared with negative control.

TABLE 7

Blood Lactic Acid Elimination after Sporting of Mice (Mean ± SD)

| | | Blood lactic acid level (mmol/L) | | | |
|---|---|---|---|---|---|
| Group | Animal number | Post sporting 0 minute (B) | Post sporting 30 minutes (C) | Difference (B − C) | P value* |
| Negative Control | 10 | 5.25 ± 1.22 | 1.58 ± 0.47 | 3.68 ± 0.91 | |
| Low | 13 | 5.68 ± 1.42 | 1.83 ± 0.97 | 3.85 ± 1.24 | >0.05 |
| Mid | 14 | 5.15 ± 1.14 | 1.92 ± 0.43 | 3.23 ± 1.14 | >0.05 |
| High | 13 | 5.60 ± 1.43 | 1.78 ± 0.61 | 3.82 ± 1.31 | >0.05 |

*Difference (B − C), compared with negative control.

1.3 Summary

The study results of antifatigue efficacy bioassay of 20(R)-ginsenoside Rg3 composition capsules in mice demonstrate that the loaded swimming time of high and low dose group mice and the pole climbing time of mid and low dose group mice are all significantly longer than those of negative controls (P<0.05); the post sporting liver glycogen level in high dose group mice are significantly higher than that of negative controls (P<0.05); the post sporting sera urea nitrogen level in high and mid dose group mice are significantly lower than that of negative controls (P<0.05); and there are no significant differences in accumulation or elimination of blood lactic acid during and post sporting in 3 treatment groups and negative control (P>0.05). According to relevant evaluation criteria, it is suggested that the test article 20(R)-ginsenoside Rg3 composition capsules has an antifatigue effect.

Example 49

The Memory Improvement Bioassay of 20(R)-Ginsenoside Rg3 Composition Capsules

1. Materials and Methods
1.1 Materials

Drug: 20(R)-ginsenoside Rg3 composition granules (10 mg/bag), supplied by Dr Fu li. Scopolamine, purchased from Chinese Testing Institute for Pharmaceuticals and Bio-pharmaceutical Products. Yiheng granules (10 mg/bag) are produced by Shanxi Kaiyuan Pharmaceuticals Co., Ltd. When use the above-mentioned products, dissolve it with saline solution to the expected concentrations.

Experimental animals: male Kunming mice, 18 to 22 grams, supplied by Pharmacy College of Jilin University.

Instruments: mouse jumping stand apparatus, water maze self manufactured by Pharmacy College of Jilin University. Contact voltage regulator, manufactured by Shanghai Zhenghua voltage regulator factory of Zhongchuan Group.

1.2 Methods
1.2.1 Step Down Procedure

Put the mice in the laboratory room for acclimation for 1 hour before experiment starts. After test session starts, the animals are put on the safe platform of the jumping stand, and acclimated to the environment for 3 minutes. After then, a 36 voltage current are switched on to the cupper grate below the platform. When the animals step down from the platform and land on the cupper grate, it will be immediately shocked, and composed of a wrong response. If it jumps back to safe area, it is a correct response. Train the animals for five minutes, and after 24 hours, the retest begins. During the formal testing, the jumping stand apparatus is switched on 36 voltage current, and animals are put on the safe platform, the wrong responses during 3 minutes are recorded.

Experimental steps: 72 healthy qualified mice, the body weights are weighed, and are assigned randomly into 6 groups, 12 mice for each group. The dosage for 20(R)-ginsenoside Rg3 composition granules are 2.16, 6.48, and 12.96 mg/kg, respectively, and the dosage for positive control Yiheng granules is 121.65 mg/kg. For blank control and model control, 0.1 ml/10 g of saline solution is dosed. All these test compounds are consecutively administered for 7 days, once daily. At 1 hour after last dosing, the blank controls are intraperitoneally injected with equal volume of saline solution, the animals in model control, Rg3 composition granule treatment groups, Yiheng granule positive control, are intraperitoneally injected with 4 mg/kg scopolamine, respectively. After 10 minutes, the step down training session begins, and will be tested again after 24 hours.

1.2.2 Water Maze Procedure

Mouse water maze apparatus is composed of a start area, a zigzag circuit with many dead-end, and a safe area (step plat). The mice are placed at start area at 1 hour after dosing, and induced to swim to safe area. Each animal is trained 10 times every day, with an interval of 25 seconds. If animals arrive at safe area in 30 seconds, it is counted as a correct response. The animals are trained continuously for 4 days. Record the number of correct response, and correct response percentage and the mean arrive time are calculated.

Experimental procedures: 72 healthy qualified mice, body weights are weighed, and are assigned randomly into 6 groups, 12 mice for each group. The dosage for 20(R)-ginsenoside Rg3 composition granules are 2.16, 6.48, and 12.96 mg/kg, respectively, and the dosage for positive control Yiheng granules is 121.65 mg/kg. For blank control and model control, 0.1 ml/10 g of saline solution is dosed. All these test compounds are consecutively administered for 10 days, once daily. At 1 hour after 7 day dosing, and 1 hour after the last day dosing the blank controls are intraperitoneally injected with equal volume of saline solution, the animals in model control, Rg3 composition granule treatment groups, Yiheng granule positive control, are intraperitoneally injected with 4 mg/kg scopolamine, respectively. After 10 minutes, the water maze training session begins. Each animal is trained 10 times every day, with an interval of 25 seconds. If animal arrive at safe area in 30 seconds, it is counted as a correct response. Record the number of correct response, and correct response percentage is calculated.

2 Results 2.1 The Improvement Effect to the Memory Acquirement Dysfunction Induced by Scopolamine (Step Down Procedure)

The study results are displayed in Table 1. Compared with blank control, the wrong response for animals in model control is significantly increased, suggesting that 4 mg/kg scopolamine have induced memory acquirement dysfunction, and the model is successful. Compared with the model control, the wrong response during testing period in 20(R)-ginsenoside Rg3 composition granules treated animals is significant decreased, and the decrease amplitude is larger than that in Yiheng granule positive control. The results demonstrate that 20(R)-ginsenoside Rg3 composition granules could improve the memory acquirement dysfunction induced by scopolamine, and the learning and memory function of mice.

TABLE 1

The Improvement Effect to the Memory Acquirement Dysfunction Induced by Scopolamine (Step Down Procedure, n = 12, Mean ± SD)

| Group | Dosage (mg/kg) | n | Wrong response |
|---|---|---|---|
| Blank control | | 12 | 0.37 ± 0.22*** |
| Scopolamine model control | | 12 | 3.8 ± 2.35 |
| Yiheng granule control | 121.65 | 12 | 0.96 ± 0.73*** |
| Rg3 composition granule | 2.16 | 12 | 0.88 ± 0.69*** |
| Rg3 composition granule | 6.48 | 12 | 0.70 ± 0.36*** |
| Rg3 composition granule | 12.96 | 12 | 0.44 ± 0.23*** |

2.2 The Improvement Effect to Space Discrimination Dysfunction Induced by Scopolamine (Water Maze Procedure)

The study results are displayed in Table 2. Compared with blank control, the correct response for animals in model control is significantly decreased. From training day 2, the correct response in 20(R)-ginsenoside Rg3 composition granules treated animals is dose dependently increased, demonstrating that 20(R)-ginsenoside Rg3 composition granules could significantly improve the space discrimination dysfunction induced by scopolamine in mice.

TABLE 2

The Improvement Effect to Space Discrimination Dysfunction Induced by Scopolamine (Water Maze Procedure, n = 12, Mean ± SD)

| Group | Dosage (mg/kg) | n | Correct response Day 2 | Day 3 | Day 4 |
|---|---|---|---|---|---|
| Blank control | | 12 | 33.11 ± 24.10 | 42.33 ± 22.14 | 52.08 ± 31.31 |
| Scopolamine model control | | 12 | 8.75 ± 7.21 | 13.45 ± 8.74 | 26.582 ± 6.52 |
| Yiheng granule control | 121.65 | 12 | 10.88 ± 6.64 | 17.95 ± 17.23 | 27.96 ± 26.47 |
| Rg3 composition granule | 2.16 | 12 | 10.98 ± 5.12 | 25.87 ± 14.52 | 52.71 ± 29.46 |
| Rg3 composition granule | 6.48 | 12 | 19.25 ± 15.34 | 35.26 ± 15.49 | 55.789 ± 23.56 |
| Rg3 composition granule | 12.96 | 12 | 27.98 ± 17.68 | 59.80 ± 26.41 | 61.58 ± 34.64 |

Example 50

The Detumescence, Pain Relieving, and Wound Healing Bioassay of 20(R)-Ginsenoside Rg3 Composition 1 Materials and Methods 1.1 Experimental Animals:

30 rats, supplied by Pharmacy College of Jilin University. Body weight, 250-300 grams, half male and half female, randomly assigned into 3 groups.

1.2 Methods 1.2.1 Animal wound model for biological evaluation: the fur in the hind leg of rats are depilated with 8% barium sulfate and refrain the skin from being damaged. After 24 hour, the rats are anesthetized by intraperitoneal injection of 30 mg/kg of 3% pentobarbital sodium, and fixed in pronation at a modeling plate. After then, a strike mallet of 1 kilogram in the modeling plate is pull up for 10 cm, and sudden perpendicularly falls down to strike the rich muscle of the femur middle of the hind leg of rat, thus a an acute soft tissue damage model is produced. Thirty minutes after the damage, a 1.5 to 3.0 cm incision is made in the wound skin, with a depth up to muscular layer, and a muscle tissue about 0.5 grams is taken out. The wound is treated correspondingly for animal groups: for the Rg3 treatment group, 20(R)-ginsenoside Rg3 composition (1 g dissolved in 1 ml of saline solution) is patched, for the positive control, Yunnan white powder (1 g dissolved in 1 ml of saline solution) painted, and for the negative control, saline solution is painted, all applications are once daily.

1.2.2 Observations: The rats are separately housed and fed according to its grouping. After post wounding awaking for 0.5 hour, the wound surface in both hind leg are lightly touched with a disposable plastic stick every 10 minutes, and pain relative behaviors such as wound licking, limb withdrawing reflex, hind leg muscle trembling at rearing, are observed for 2 hours, totally 12 times touches. The general wound healing status is photographed at day 3 and 7 after wounding, and wound infection is recorded. At day 7 after wounding, the animals are euthanized and weighed, to assess the changes of the body weight.

1.2.3 Statistic analysis: The enumeration data is analyzed by $X^2$ test, and the measurement data is analyzed by Analysis of Variance, with a SPSS 8.0 software. The significant level is set as $P<0.05$.

2 Results
2.1 Pain Relative Behaviors During 2 Hours Awaking Period in Different Groups After analysis of variance, in general significant differences ($p<0.05$) in the pain relative behaviors, such as wound licking, limb withdrawing reflex, hind leg muscle trembling at rearing, are observed among 3 groups (Table 1). After pairwise comparison, for the wound licking, 20(R)-ginsenoside Rg3 composition treatment group is significantly different ($p<0.05$) from the Yunnan white powder positive control and the saline solution negative control; for the limb withdrawing reflex and hind leg muscle trembling at rearing, there are no significant differences ($p>0.05$) among 3 groups. These results demonstrate that ginsenoside Rg3 composition have analgesic effect, and its efficacy is better than that of Yunnan white powder.

2.2 Tissue Wound Infection after Damage in Both Hind Legs of Rats

After $X^2$ test, there are significant difference in wound infection among 3 groups ($p<0.01$), suggested that ginsenoside Rg3 composition have anti-infection effects, the wound infection rate in Rg3 composition treatment group are significantly lower than that in the Yunnan white powder positive control and the saline solution negative control.

2.3 The Overall Status for Wound Healing in Different Group

After direct observation of the wound in day 3 after damage, the wounds in rats of ginsenoside Rg3 composition group are dry, without exudates, and the skin around the wound is obviously shrunk. But the wounds in rats of Yunnan white powder positive control have some discharge, and the skin around the wounds is slight shrunk. And the wounds in rats of saline solution negative control have bulky discharge, enlarged wound surface, and the skin around the wounds has some pussy scar. In the day 7 after damage, the wounds in rats of ginsenoside Rg3 composition group are dry, without infection, and are complete filled by granulation tissue, and the epithelization de novo is obviously observed. For the wounds in rats of Yunnan white powder positive control, the wound surface area are shrunk, some exudates and a thin layer of granulation tissue are observed, but no epithelization de novo is obviously observed. For the wounds in rats of saline solution negative control, bulky exudates are observed, the wound surface areas are not shrunk, and some ulcer surfaces are formed. From the above observation, it could be concluded that ginsenoside Rg3 composition have some effects on the detumescence, bacteriostasis, and wound healing, with a better efficacy than Yunnan white powder and normal sodium controls.

TABLE 1

Comparison on the Pain Relative Behaviors among 3 Groups

| Group | n | Wound licking | Limb withdrawing reflex | Muscle trembling |
|---|---|---|---|---|
| Saline solution control | 10 | 1.30 ± 1.50 | 0.70 ± 1.11 | 5.30 ± 3.16 |
| Yunnan white powder | 10 | 9.00 ± 2.16 | 9.40 ± 2.59 | 10.70 ± 1.33 |
| Ginsenoside Rg3 composition | 10 | 11.20 ± 0.92 | 11.40 ± 0.84 | 10.40 ± 1.43 |

*Rg3 comparing to other two groups $p < 0.01$

TABLE 2

Comparison on the Infection Rates among 3 Groups

| Group | Infected wound | Not infected wound | Total |
|---|---|---|---|
| Saline solution control | 1 | 19 | 20 |
| Yunnan white powder | 17 | 3 | 20 |
| Ginsenoside Rg3 composition | 8 | 12 | 20 |

*$p < 0.01$

What is claimed is:

1. An aqueous solution of a medicinal composition comprising a 20(R)-ginsenoside Rg3, wherein the solution consists of 20(R)-ginsenoside Rg3, arginine, and water, wherein the content of the ginsenoside Rg3 in the solution is 0.5~10 mg/ml, and the weight ratio of the 20(R)-ginsenoside Rg3 to the arginine is 1:1~300.

2. The aqueous solution according to claim 1, wherein the solution is prepared by a process comprising step 1, step 2, step 3 and step 4,
    wherein step 1 comprises dissolving the 20(R)-ginsenoside Rg3 in an organic solvent or a mixture of organic solvents, and forming a solution comprising 0.1~5% the ginsenoside;
    wherein step 2 comprises forming an aqueous solution of arginine;
    wherein step 3 comprises adding all the ginsenoside solution obtained in step 1 in whole into the aqueous solution of arginine obtained in step 2 at 40~100° C. where the ratio of 20(R)-ginsenoside Rg3 to arginine=1:1~300, and stirring the mixture for 0.1~3 hour to obtain a clear solution; and
    wherein step 4 comprises removing the solvent from the clear solution obtained in step 3 at temperature of 80~100° C. under a vacuum of 0.01~0.08 MPa until the solution reaches a near dryness state of about ⅔ of the original volume, adding water to the solution of the near dryness state to the original volume prior to removing the solvent, removing the solvent at temperature of 80~100° C. under a vacuum of 0.01~0.08 MPa; repeating the previous procedure twice to form a near dryness material, and adding injection water or purified water into the near dryness material to form a solution.

3. A method of treating a patient in need of improvement of human memory, resistance to the fatigue, and wound healing, including relief of pain and/or detumescence associated with the wound, comprising administering to the patient a therapeutically effective amount of the aqueous solution according to claim 1.

4. A method of treating a patient in need of improvement of human memory, resistance to the fatigue, and wound healing, including relief of pain and/or detumescence associated with the wound, comprising administering to the patient a therapeutically effective amount of the according to claim 2.

5. The aqueous solution according to claim 1, wherein the content of the ginsenoside Rg3 in the solution is 2 mg/ml.

6. The aqueous solution according to claim 1, wherein the content of the ginsenoside Rg3 in the solution is 1 mg/ml.

\* \* \* \* \*